(12) United States Patent
Miller et al.

(10) Patent No.: US 11,280,782 B2
(45) Date of Patent: Mar. 22, 2022

(54) POLYMER MICROPARTICLE-BASED METHOD FOR PROBE DEPOSITION IN LABEL-FREE BIOSENSORS

(71) Applicants: UNIVERSITY OF ROCHESTER, Rochester, NY (US); ADARZA BIOSYSTEMS, INC., West Henrietta, NY (US)

(72) Inventors: Benjamin L. Miller, Penfield, NY (US); Mark A. Lifson, Rochester, NY (US); Jared A. Carter, West Henrietta, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 48 days.

(21) Appl. No.: 15/546,737

(22) PCT Filed: Feb. 8, 2016

(86) PCT No.: PCT/US2016/016958
§ 371 (c)(1),
(2) Date: Jul. 27, 2017

(87) PCT Pub. No.: WO2016/127163
PCT Pub. Date: Aug. 11, 2016

(65) Prior Publication Data
US 2018/0052156 A1 Feb. 22, 2018

Related U.S. Application Data

(60) Provisional application No. 62/113,241, filed on Feb. 6, 2015.

(51) Int. Cl.
*G01N 33/543* (2006.01)
*G01N 33/545* (2006.01)

(52) U.S. Cl.
CPC ..... *G01N 33/54366* (2013.01); *G01N 33/545* (2013.01); *G01N 33/5432* (2013.01); *G01N 33/54313* (2013.01); *G01N 33/54373* (2013.01)

(58) Field of Classification Search
CPC ......... G01N 33/54313; G01N 33/5432; G01N 33/54346–33/54353; B01L 2300/0819
See application file for complete search history.

(56) References Cited

U.S. PATENT DOCUMENTS

| | | | | |
|---|---|---|---|---|
| 7,935,518 | B2 * | 5/2011 | Luchini | B01D 15/34 422/422 |
| 2006/0040407 | A1 | 2/2006 | Falcovitz-Gerassi et al. | |
| 2006/0127931 | A1 * | 6/2006 | Schmidt | B82Y 5/00 435/6.19 |
| 2010/0279886 | A1 | 11/2010 | Fauchet et al. | |
| 2014/0329229 | A1 * | 11/2014 | Lepene | G01N 33/543 435/5 |
| 2015/0037815 | A1 | 2/2015 | Miller et al. | |

FOREIGN PATENT DOCUMENTS

| | | | | |
|---|---|---|---|---|
| DE | 102007049930 A1 * | 4/2009 | | B82Y 10/00 |
| EP | 2752664 A1 | 7/2014 | | |
| WO | 2000079268 A2 | 12/2000 | | |
| WO | 2003/040700 A1 | 5/2003 | | |
| WO | 2003040700 A1 | 5/2003 | | |
| WO | 2006102687 A1 | 9/2006 | | |

OTHER PUBLICATIONS

Iyer et al. "Development of Environmentally Responsive Hydrogels with Metal Affinity Behavior" Journal of Applied Polymer Science, vol. 105, 1210-1220 (2007), DOI 10.1002/app.26294 (Year: 2007).*
Carter et al., "A label-free, multiplex competitive assay for small molecule pollutants", Biosensors and Bioelectronics 77 (2016) 1-6 (Year: 2016).*
Sriram et al. "Validation of Arrayed Imaging Reflectometry Biosensor Response for Protein-Antibody Interactions: Cross-Correlation of Theory, Experiment, and Complementary Techniques", Anal. Chem. 2011, 83, 3750-3757, dx.doi.org/10.1021/ac2001302.*
International Search Report and Written Opinion corresponding to PCT/US2016/016958, dated May 24, 2016.
Su et al., "Microgel-based Inks for Paper-Supported Biosensing Applications," Biomacromolecules 9:935-941 (2008) abstract only.
Examination Report in EP 16709169.3, dated May 12, 2021.
Lifson et al., "Functionalized Polymer Microgel Particles Enable Customizable Production of Label-Free Sensor Arrays," Anal Chem 87(15):7887-93 (2015).
Guan and Zhang, "PNIPAM Microgels for Biomedical Applications: From Dispersed Particles to 3d Assemblies," Soft Matter 7:6375-6384 (2011).
Zhang et al., "Ultrathin Hydrogel Films for Rapid Optical Biosensing," Biomacromolecules 13:92-97 (2012).

* cited by examiner

*Primary Examiner* — Rebecca M Giere
*Assistant Examiner* — Xiaoyan Zou
(74) *Attorney, Agent, or Firm* — Troutman Pepper Hamilton Sanders LLP

(57) ABSTRACT

Disclosed is a sensor chip for detecting a target molecule in a sample. The sensor chip includes a substrate having a surface and a layer of hydrogel particles immobilized on the substrate surface at two or more locations on the surface, wherein the hydrogel particles at a first location comprise a plurality of first probe molecules bound to the particles and the hydrogel particles at a second location comprise a plurality of second probe molecules bound to the particles. Systems that include the sensor chip, as well as methods of preparing and using the sensor chip, are also disclosed.

11 Claims, 13 Drawing Sheets

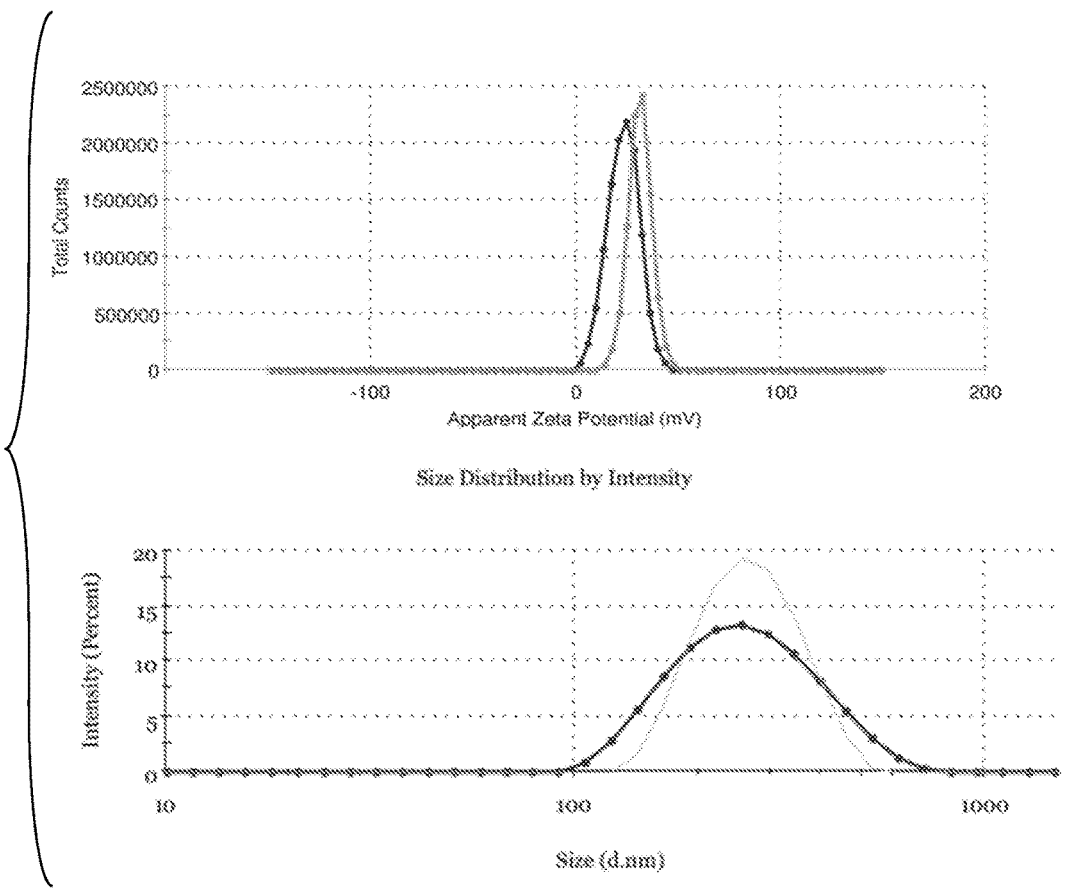
FIG. 5
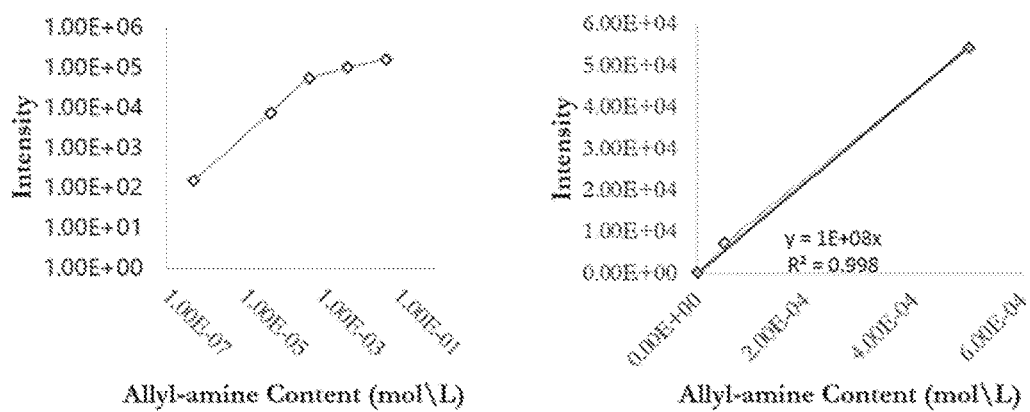
FIG. 6A
FIG. 6B

*FIG. 9A*
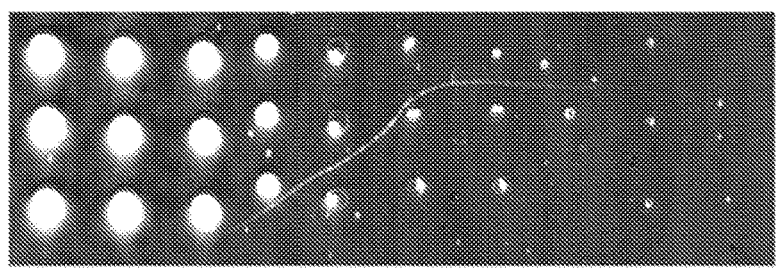
*FIG. 9B*
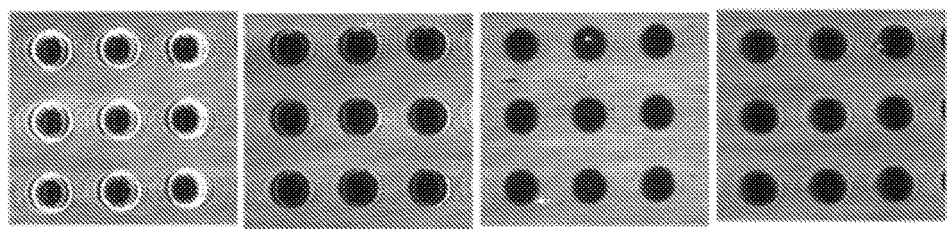
*FIG. 9C*
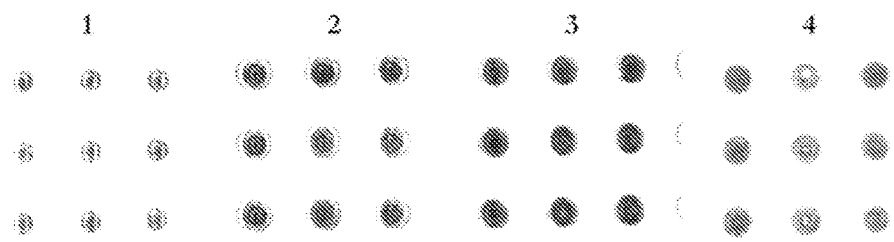
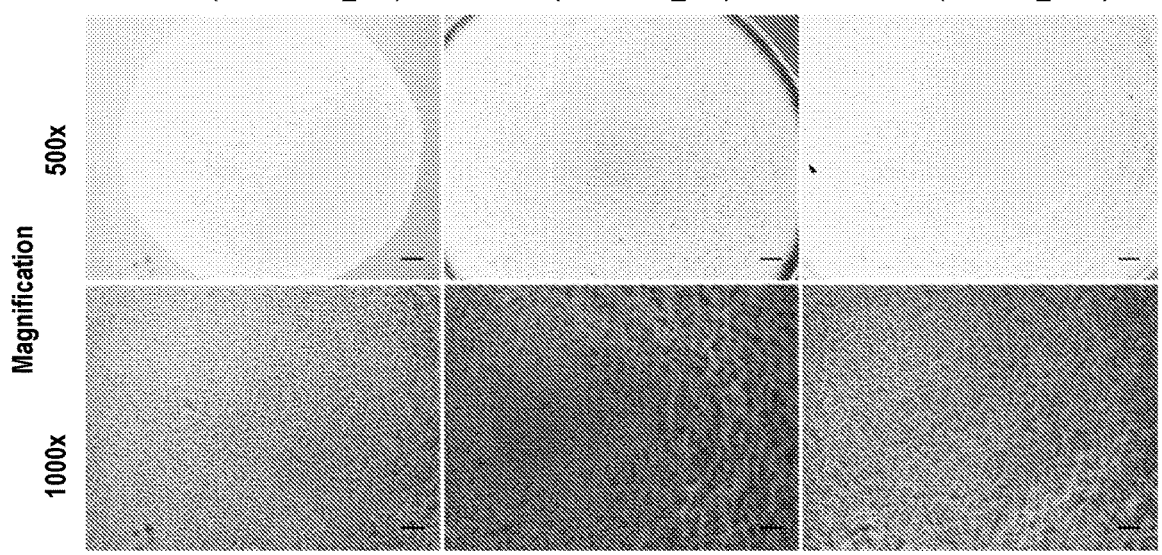
*FIG. 10*

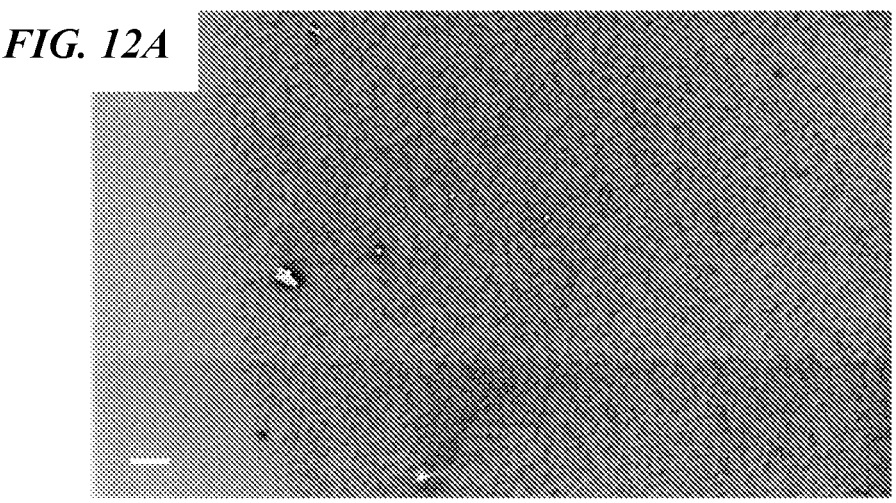
FIG. 12A
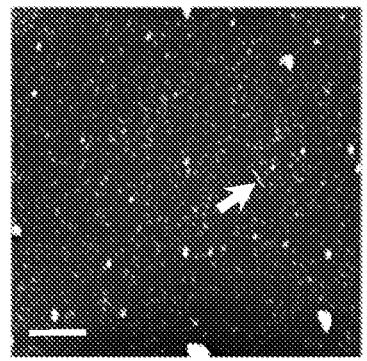
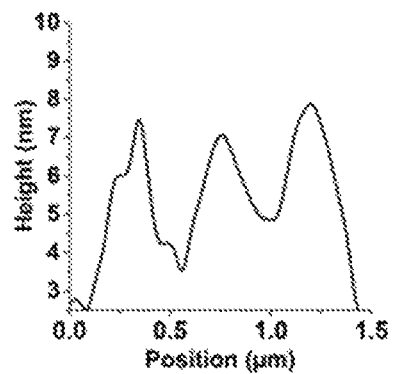
FIG. 12B
FIG. 12C

BSA, AWB, Water

BSA, PBS, Water

PBS, PBS, Water anti-human biotinylated TNF-α
PBS (15 min) w/ shaking
Water (15 min) w/ shaking anti-human biotinylated TNF-α
1% BSA (no shaking)
PBS (15 min) w/ shaking
Water (15 min) w/ shaking FIG. 20A
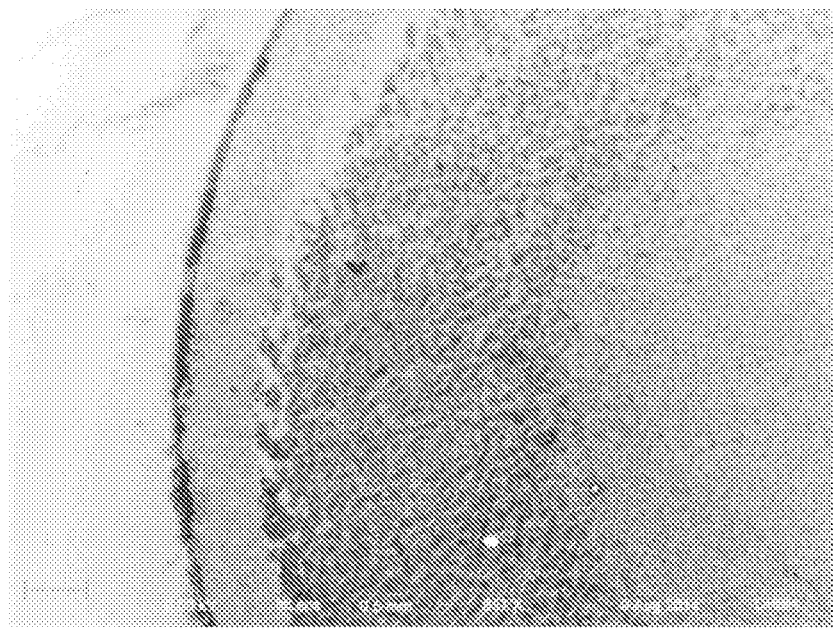
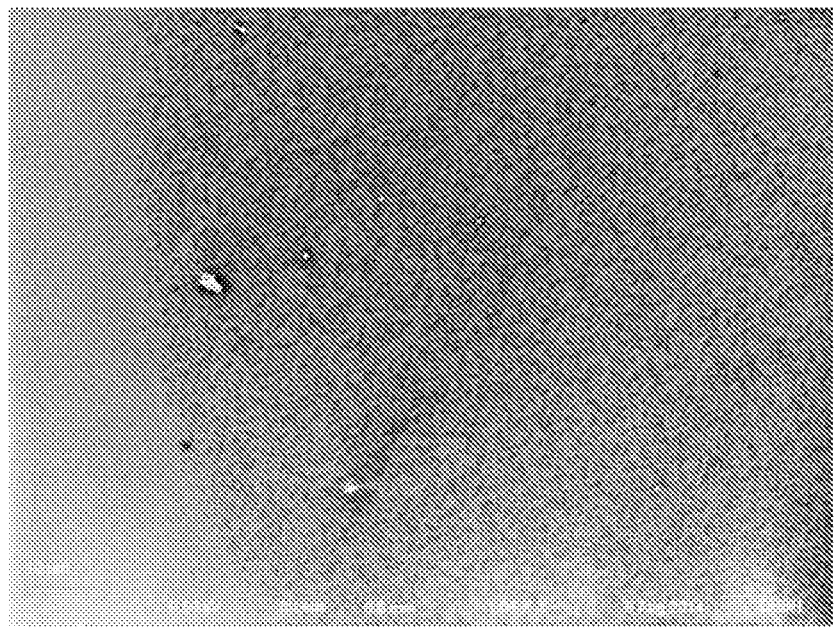
FIG. 20B

POLYMER MICROPARTICLE-BASED METHOD FOR PROBE DEPOSITION IN LABEL-FREE BIOSENSORS

This application is a national stage application under 35 U.S.C. § 371 of PCT Application No. PCT/US2016/016958, filed Feb. 8, 2016, which claims the benefit of U.S. Provisional Patent Application Ser. No. 61/113,241, filed Feb. 6, 2015, which is hereby incorporated by reference in its entirety.

This invention was made with government support under grant GM100788 awarded by the National Institutes of Health. The government has certain rights in the invention.

TECHNOLOGICAL FIELD

This application relates to a polymer microparticle-based method for antibody deposition in label-free biosensors, the resulting devices formed thereby, and biological sensors containing the same.

BACKGROUND

There is a significant interest in developing microarray technologies to monitor the presence, amounts, and activities of many different proteins. The diagnostic applications of these devices were first envisioned by Roger Ekins, who posited that there would be remarkable improvements in accuracy and sensitivity when the interaction area of the target and receptor were reduced (Parpia et al., *Anal. Biochem.* 401:1-6 (2010); Ekins, R. P., *Clin. Chem.* 44:2015-2030 (1998); Ekins et al., *Clin. Chem.* 37:1955-1967 (1991)). Since then, there has been a major effort to immobilize hundreds to thousands of proteins on a single device to globally analyze the binding of targets in a high-throughput manner (MacBeath et al., *Science* 289:1760-1763 (2000); MacBeath, G., *Nat. Genet.* 32:526-532 (2002); Robinson et al., *Nat. Med.* 8:295-301 (2002); Stoll et al., *Front. Biosci.* 7:C13-C32 (2002); Zhu et al., *Curr. Opin. Chem. Biol.* 7:55-63 (2003)).

A microarray consists of a rigid support, on which biomolecules are immobilized in an addressable way, so that each printed region (spot) is specific for one target in a sample of interest. In this format, a wide variety of proteins can be targeted by immobilizing different probe biomolecules including proteins, peptides, antibodies, sugars, enzymes, or aptamers (MacBeath, G., *Nat. Genet.* 32:526-532 (2002); Stoll et al., *Front. Biosci.* 7:C13-C32 (2002); Falsey et al., *Bioconjug. Chem.* 12:346-353 (2001); Houseman et al., *Nat. Biotechnol.* 20:270-274 (2002)). Binding of the target is most often detected by measuring fluorescence intensity changes from labeled tags either on the target itself (direct mode), or on a 2° antibody (sandwich). Alternatively, new microarray formats have been developed that directly measure target concentrations via changes in the optical properties of the sensor itself as a function of bound target. These label-free technologies can have high sensitivities, but many require regular and uniform deposition of capture molecules, as compared to fluorescent methods, which are insensitive to localized variability in the z direction (Dufva, M., *Biomol. Eng.* 22:173-184 (2005); Brown et al., *Proc. Natl. Acad. Sci. U.S.A.* 98:8944-8949 (2001)). Regardless of the type of assay, the surface functionalization and immobilization procedures must be carefully considered since these directly affect the probe density and their orientation on the substrate, which in turn affects the amount of target bound (Xu et al., *J. Phys. Chem. B* 110:1907-1914 (2006); Kosaka et al., *Analyst* 138:863-872 (2013); Chen et al., *Langmuir* 19:2859-2864 (2003)). It has been observed that directly immobilizing biomolecules onto planar surfaces results in significant unfolding/denaturing of proteins, translating to a loss of ligand binding activity which affects the assay's sensitivity and its ultimate performance (Butler et al., *J. Immunol. Methods* 150:77-90 (1992); O'Brien et al., *Anal. Chem.* 72:703-710 (2000); Ibii et al., *Anal. Chem.* 82:4229-4235 (2010)). Thus, increasing the density and integrity of probe molecules on planar surfaces is an important subject of research. One approach to increase antibody density onto surfaces is to incorporate them within a 3D matrix as opposed to a 2D surface.

Hydrogels possess high surface areas, biocompatibility, and afford simple bioconjugation to proteins or other probe molecules. By providing a more "solution-like" environment for attached probe molecules, hydrogels may also reduce surface-induced denaturation (Buenger et al., *Prog. Polym. Sci.* 37:1678-1719 (2012)). Hydrogels are typically applied to substrates in one of two ways: either the network is coated prior to biomolecule immobilization, or, hydrogel precursors are spotted with biomolecules and polymerized in situ (Byun et al., *Lab Chip* 13:886-89 (2013); Angenendt, P., "Progress in Protein and Antibody Microarray Technology," *Drug Discovery Today* 10:503-511 (2005); Sugaya et al., *Langmuir* 28:14073-14080 (2012); Massad-Ivanir et al., *Adv. Funct. Mater.* 20:2269-2277 (2010); Wilkins Stevens et al., *Anal. Chem.* 75:1141-1146 (2003); Zubtsov et al., *Anal. Biochem.* 368:205-213 (2007); Rubina et al., *Biotechniques* 34:1008-1022 (2003); Rubina et al., *Anal. Biochem.* 340: 317-329 (2005)). However, many label-free microarray technologies are incompatible with these processes, since they produce thick hydrogel layers with significant variations in coating thickness and porosity (Olle et al., *J. Exp. Mol. Pathol.* 79:206-209 (2005); Charles et al., *Biosens. Bioelectron.* 20:753-764 (2004); Derwinska et al., *Anal. Biochem.* 370:38-46 (2007)). This is a major reason why ultra-sensitive methods continue to use 2D immobilization strategies for capture molecules (Feuz et al., *ACS Nano* 4:2167-2177 (2010); Pal et al., *Biosens. Bioelectron.* 44:229-234 (2013); Ishikawa et al., *Mol. Cell. Probes* 5:81-95 (1991); Waggoner et al., *Lab Chip* 7:1238-1255 (2007); Vollmer et al., *Appl. Phys. Lett.* 80:4057 (2002)). Both strategies also limit the degree to which probe molecule deposition may be optimized on a probe-by-probe basis. The pre-existing hydrogel matrix strategy is limited since the underlying substrate is the same for all probes, and the post-spotting polymerization strategy is constrained by the requirements of the polymerization reaction.

The devices and methods disclosed herein are directed to overcoming these and other deficiencies in the art.

SUMMARY

A first aspect relates to a sensor chip for detecting a target molecule in a sample. The sensor chip includes a substrate having a surface and a layer of hydrogel particles immobilized on the substrate surface at two or more locations on the surface, wherein the hydrogel particles at a first location comprise a plurality of first probe molecules bound to the particles and the hydrogel particles at a second location comprise a plurality of second probe molecules bound to the particles.

A second aspect relates to a detection system that includes a sensor chip of the first aspect, a light source that is positioned to illuminate the sensor chip, and a detector that is positioned to detect light reflected or emitted from the surface of the sensor chip, and thereby determine whether a target molecule is present in a sample exposed to the surface of the sensor chip.

A third aspect relates to a method for sensing a target molecule in a sample that involves providing a detection system according to the second aspect, directing light at a surface of the sensor chip, contacting the sensor chip with a sample under conditions effective to allow a target molecule in the sample to bind specifically to one of the first and second probe molecules, and detecting light reflected or emitted by sensor chip to identify the presence of a target molecule in the sample.

A fourth aspect relates to a method for preparing a sensor chip that involves providing a substrate having a surface upon which a layer of hydrogel particles are immobilized at two or more locations on the surface, the hydrogel particles comprising probe molecules bound to the particles, washing the substrate surface with a wash medium, and drying the substrate.

As demonstrated in the accompanying Examples, a new technique was developed to deposit thin and reproducible hydrogel layers onto rigid surfaces for optical label-free microarrays using Poly (N-Isopropylacrylamide) (PNIPAM) particles conjugated with capture (or probe) molecules. These particles self-assemble into highly reproducible and uniform self-assembled monolayers upon drying after microprinting on a substrate. Here, PNIPAM hydrogel particles were co-polymerized with allylamine (AA) so that after synthesis, free amines could be covalently linked with biotin using an amine-reactive functional group (N-hydroxysuccinimide). Upon addition of avidin with the particles, biotinylated probe molecules were linked to the particles in a single conjugation step in a "sandwich" format. Alternatively, probe molecules were covalently linked to the free amines of the hydrogel particles. These methods are highly modular and can be used to create a library of particle-probe entities, which will allow formation of high density arrays.

A highly sensitive protein microarraying technology, Arrayed Imaging Reflectometry (AIR), was used to evaluate the performance of hydrogel particle microarrays. AIR operates by monitoring the light intensity of an angled beam reflected off of a flat substrate, which is composed of a protein-reactive film on a thermally grown silicon oxide layer. If the angle, wavelength, and polarization of the incident light beam is fixed, a near-zero reflectance condition can be obtained by adjusting the thickness of the thermally grown oxide (e.g., $SiO_2$ on Si). The relationship between the intensity of reflection and thickness has been well characterized both experimentally and theoretically and enabled quantitative evaluation of biological systems including affinity constants for antibodies and targets (Lu et al., *J. Anal. Chem.* 76:4416-4420 (2004); Horner et al., *Biosens. Bioelectron.* 21:1659-1663 (2006); Mace et al., *Biosens. Bioelectron.* 24:334-337 (2008); Carter et al., *Biosens. Bioelectron.* 26:3944-3948 (2011); Mace et al., *Talanta* 83:1000-1005 (2011); Yadav et al., *Anal. Chem.* 86:1067-1075 (2014), the disclosures of which are incorporated herein by reference in their entirety). Though the Examples discuss the specifics of applying a hydrogel network onto AIR substrates, the methods, materials, and techniques can be easily applied to other label-free sensor technologies that utilize thin and uniform hydrogel films. Similarly, this approach can also be used for labeled microarray technologies.

BRIEF DESCRIPTION OF THE DRAWINGS

FIG. 5 is a pair of graphs showing dynamic light scattering measurements (top graph) of PNIPAM-co-allylamine before (gray line) and after biotinylation (black line). Zeta potential measurements for these particles are shown for PNIPAM-co-allylamine (bottom graph) before (gray line) and after biotinylation (black line).

FIGS. 6A-6B are a pair of graphs showing an o-phthalaldehyde assay evaluating amine content for PNIPAM-co-allylamine and PNIPAM-co-allylamine-biotin nanoparticles. Calibration curve with allylamine consisted of two linear regions (FIG. 6A), which was fit with a best-fit line for the intensity regions measured for PNIPAM-co-allylamine particles (FIG. 6B).

FIGS. 9A-9C show AIR images illustrating spot morphology differences as a function of microgel particle concentration deposited using a piezo microarrayer. PNIPAM was deposited in dilutions of 1/2 to 1/2048 in 2n increments onto toluene washed $SiO_2$ surfaces (FIG. 9A, top). PNIPAM-co-allylamine was deposited in dilutions of 1/40 (panel 1, FIGS. 9B and 9C), 1/60 (panel 2, FIGS. 9B and 9C), 1/80 (panel 3, FIGS. 9B and 9C), and 1/100 (panel 4, FIGS. 9B and 9C) onto octadecylmethyldiethoxysilane (ODMDES) functionalized $SiO_2$ surfaces and imaged at AIR at 100 ms (FIG. 9B) and 250 ms (FIG. 9C) exposure lengths.

FIG. 10 is a panel of brightfield images showing PNIPAM particle packing behavior on $SiO_2$ surfaces functionalized with either octadecyltrichlorosilane (OTS), trimethylchlorosilane (TCS), or washed with toluene. Contact angle measurements are shown to the right of the silane name. Images were captured at 500× magnification (top), or 1000× (bottom). Scale bars are 1 μm for 500× and 0.5 μm for 1000×.

FIGS. 12A-12C show morphological analysis of dry, self-assembled PNIPAM-avidin particles after deposition with a piezo-microarrayer (~300 pL volume droplet). Scanning Electron Microscopy (SEM) image showing a droplet edge (FIG. 12A) indicated densely packed particles in a monolayer. Atomic Force Microscopy (AFM) analysis of the surface (FIG. 12B) corroborated the packing behavior of the dried particle droplets observed with SEM, and a profile of a small portion of the surface (white arrow) indicated that the particles flattened to ~500 nm widths and ~4 nm heights (FIG. 12C). Scale bars (in 12A, 12B) are 5 µm.

FIG. 13A was a standing bovine serum block (30 min.) followed by shaking for 15 min. in assay wash buffer (contains surfactant), followed by a shaking 15 min. water wash. FIG. 13B was a standing bovine serum albumin block (30 min.) and shaking buffer and water washes (15 min). FIG. 13C was a standing buffer incubation (30 min.) followed by a shaking 15 min. buffer wash, and a shaking 15 min. water wash. The spot intensities for substrates exposed to the different wash conditions were measured using AIR and converted to thickness readings (FIG. 13D).

FIGS. 20A-20B show SEM spot edge images of PNIPAM-co-allylamine-biotin-avidin particle spots diluted in ddH2O (FIG. 20A) or mPBS (FIG. 20B).

DETAILED DESCRIPTION

A first aspect relates to a sensor chip for detecting a target molecule in a sample. The sensor includes a substrate having a surface and a layer of hydrogel particles immobilized on the substrate surface at two or more locations on the surface, wherein the hydrogel particles at a first location comprise a plurality of first probe molecules bound to the particles and the hydrogel particles at a second location comprise a plurality of second probe molecules bound to the particles.

The arrays can include fewer than $10^2$ locations, more than $10^2$ locations, more than $10^3$ locations, more than $10^4$ locations, more than $10^5$ locations, and in certain embodiments more than $10^6$ locations. These locations are also commonly referred to as "spots".

The different locations can include the same probe molecules but in different concentrations and can be repeated for each of a plurality of probe molecules.

The overall design and construction of the sensor chip can be varied according to the particular detection system in which it is to be employed. These include, for example and without limitation, sensors designed for use with Arrayed Imaging Reflectometry ("AIR") detection system, Surface Plasmon Resonance ("SPR") detection system, Brewster Angle Straddle Interferometry ("BAST") detection system, Interferometric Reflectance Imaging Sensor ("IRIS") detection system, or ellipsometry detection system, as well as any other label-free or fluorescence labeled array technique.

While AIR using s-polarized light has proven to be a highly sensitive, simple analytical method for the quantitative detection of a variety of biomolecular analytes, the system described in the above-referenced U.S. Pat. No. 7,292,349 to Miller et al. (the disclosure of which is incorporated herein by reference in its entirety) is much more easily carried out in a dry state, that is, with an air/oxide interface rather than with an aqueous/oxide interface.

Figure 1:
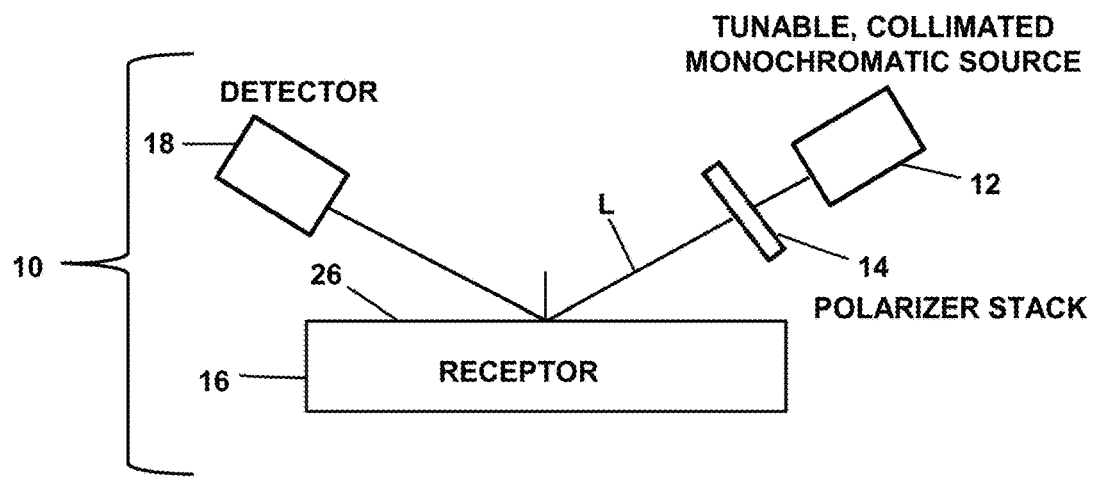
FIG. 1 is a schematic illustration of an AIR detection system.

An AIR detection system 10 is illustrated in FIG. 1. The detection system 10 includes a light source 12, a polarizer 14, a receptor 16, and a detector 18, although the system can have other types and arrangements of components. The light source 12 in the detection system 10 generates and transmits a light L at a set wavelength towards a surface 26 of the receptor 16. In this particular embodiment, the light source 12 is a tunable, collimated, monochromatic light source. The medium in which the light L travels from the light source 12 and polarizer 14 to the receptor 16 is air. The polarizer 14 is positioned in the path of the light from the light source 12 and polarizes the light in a single direction. The detector 18 is positioned to measure the reflected light from the receptor 16. In this particular embodiment, the detector 18 measures the amplitude of the reflected light at a single polarization and ignores phase.

Figure 2:
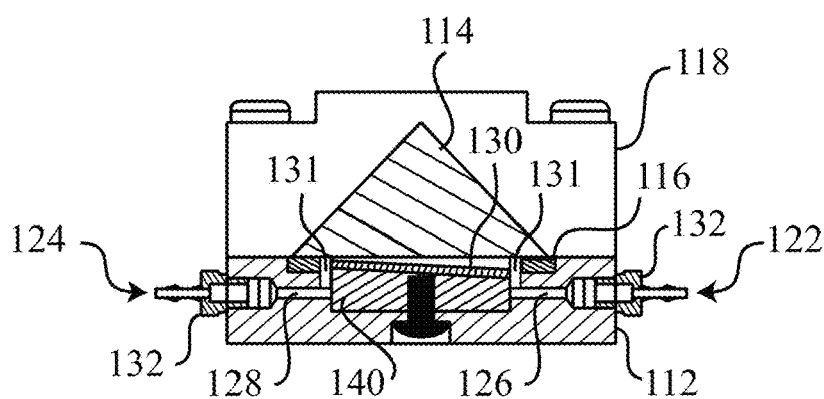
FIG. 2 is a cross-sectional view a flow cell of the invention which includes a sensor chip suitable for use in an AIR detection system for aqueous environments.

An improved system for performing AIR in an aqueous environment is described in U.S. Pat. No. 8,502,982 to Mace et al., and PCT International Patent Application No. PCT/US2008/081804 to Mace et al., the disclosures of which are incorporated herein by reference in their entirety. Basically, the flow cell as described therein allows for coupling of the s-polarized light into the aqueous environment for detection of target binding. One embodiment of the flow cell is illustrated in FIG. 2. The flow cell includes a base 112, a light transmissive cover 114 in the form of a 90° prism, a gasket 116 positioned between the base and cover, and one or more mounting braces 118 that are utilized to secure the base and cover in a substantially fluid-tight manner. The base 112 includes a well 120 formed in one face thereof, as well as inlet 122 and outlet 124 that communicate with the well via passages 126 and 128, respectively. Inlet 122 and outlet 124 are formed on opposite ends of the base such that the passages 126 and 128 that communicate with the well 120 ensure fluid flow over chip 130 when it is placed in the well. To assist with fluid flow in this respect, a notch 131 is formed in the sidewall of well 120 at each end of the well such that fluid can easily flow into the well from passage 126 and from the well via passage 128. The passages 126 and 128 are preferably provided with fittings 132 that allow conduits or other forms of tubing to be coupled to the flow cell. For example, the fluid sample source can be coupled to the inlet 122 and the outlet 124 can be coupled to additional fluid analyzers or simply to a waste reservoir. The chip 130 is preferably supported in the well 120 by an angled chip support 140.

In both the wet and dry AIR systems, the sensor chip has the same fundamental construction with a substrate and one or more coating layers on the substrate. As described in the above-referenced U.S. Pat. No. 7,292,349 to Miller et al., U.S. Pat. No. 8,502,982 to Mace et al., and PCT International Patent Application No. PCT/2008/081804 to Mace et al., a number of different materials can be selected for the substrate and coating(s). Any suitable combination of substrates and coatings is contemplated for the sensor chip to be used in an AIR detection system. In one embodiment, the substrate includes a Si substrate and a $SiO_2$ coating with high uniformity and low surface roughness of less than 1 nm across the surface of the chip.

In certain embodiments, the AIR sensor chip affords a condition of near perfect destructive interference for light reflected from the chip surface in the absence of target binding and a quantity-dependent increase in light reflected from the chip surface in the presence of target binding. As used herein, the condition of near perfect destructive interference indicates than the reflectivity is less than $10^{-3}$, more preferably less than $10^{-4}$, or less than $10^{-5}$, or even less than $10^{-6}$ in the absence of target binding.

The BASI detection system is described in U.S. Patent Publication No. 20070076214 to Rothberg, the disclosure of which is incorporated herein by reference in its entirety. The BASI system, like the AIR system, exploits interference between reflections from the medium/coating and coating/substrate interfaces, and exhibits changes in reflectivity upon binding of biomolecules to the coating. The basic design of the system is similar to that illustrated in FIG. 1 (for AIR), but the structure of the sensor chip differs. The BASI system is functional with any substrate/coating combinations where the coating is very thin (e.g., a native oxide film on silicon) and when the incidence angle on one of two interfaces (substrate/coating or coating/medium) is greater than its Brewster angle and the incidence angle on the other of the two interfaces is less than its Brewster angle. Unlike AIR systems being commercially developed for use with incident s-polarized light, the BASI system relies on the detection with p-polarized light. As a result of using Brewster angle straddle and p-polarized light, where the coating thickness is $\ll\lambda$, a phase flip of the reflected polarization allows nearly complete destructive interference (where reflectivity is preferably less than about $10^{-4}$ or even $10^{-5}$ in the absence of target binding).

Figure 3:
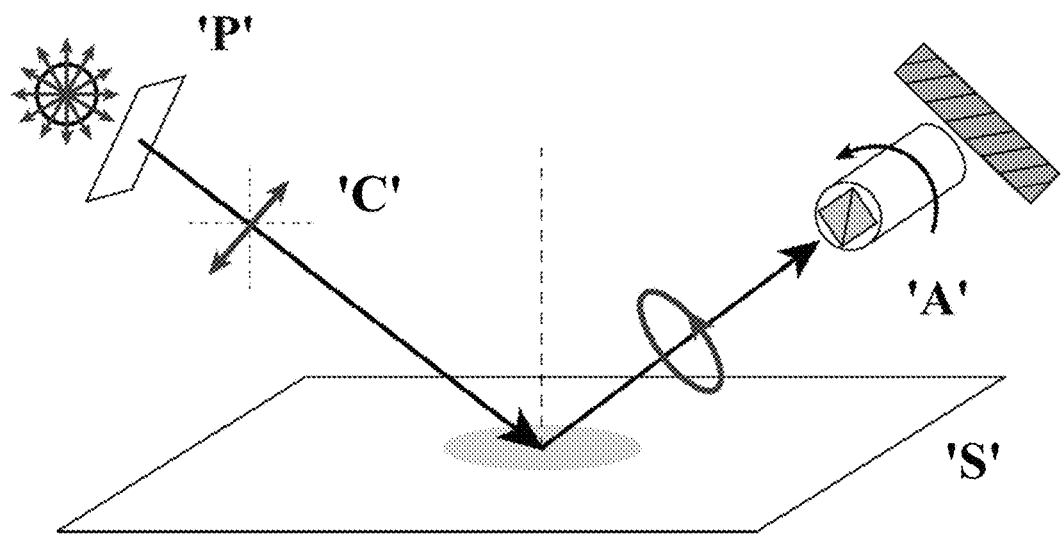
FIG. 3 is a schematic illustration of an ellipsometry detection system.

Ellipsometric detection systems measure the polarization component of reflected light as a measure of changes in coating thickness on the surface of the sensor chip. Ellipsometry sensitively measures the change of the state of polarization when electromagnetic radiation is reflected or transmitted by a sample. A classical embodiment of such an ellipsometric detection system, illustrated in FIG. 3, includes a light source that emits a collimated light beam passing a variable polarization controller given by the combination of a linear polarizer (P) and a compensator in the form of a quarter-wave plate (C). The polarized light beam is incident on the sensor surface (S) under a known oblique angle, reflected from the sample surface and analyzed by a second linear polarizer coupled to a suitable photodetector (A, collectively). In this ellipsometer setup, the measurement may be done by changing the azimuths of the components P and A, while the optical axis of C is kept at a constant azimuth, e.g., at 45° with respect to the plane of incidence, until the photodetector receives a minimum of intensity. The azimuthal angles of the components P, C and A for this "nulling" condition may be used to calculate the ellipsometric angles Delta and Psi, which are specific for the optical parameters of the sample at a given angle of incidence and wavelength of light. Using a suitable optical model and numerical regression, the quantities Delta and Psi may be recalculated in terms of the thickness of the optical layer, or changes thereof during a growth process. The application of ellipsometry for monitoring of binding reactions of biological molecules dates back to 1942 (Rothen et al., "Serological Reactions of Protein Films and Denatured Proteins," *J Exp Med* 76:437-450 (1942), the disclosure of which is incorporated herein by reference in its entirety), where the amount of adsorbed biological material at a surface during a binding reaction may be recalculated from the quantities Delta and Psi.

Imaging ellipsometry, as described for example in U.S. Pat. No. 5,076,696 to Cohn et al., the disclosure of which is incorporated herein by reference in its entirety, uses spatially resolving detector and imaging optics to allow for a massively parallel measurement of ellipsometric data, e.g., in the form of Delta and/or Psi maps. Such maps may in turn be converted into surface maps of layer thickness, optical index of refraction, chemical composition or the amount of adsorbed material for each spot on an array. Imaging ellipsometry with its intrinsic parallel detection scheme may be used advantageously as a detection technique for these so-called biochips, microarrays or microplates (Eing et al., *Imaging Ellipsometry in Biotechnology*, ISBN 3-9807279-6-3 (2002), the disclosure of which is incorporated herein by reference in its entirety).

Imaging ellipsometry has been demonstrated with light employed for the measurement impinging on the surface to be measured coming from the ambient medium. Other measurement setups are based on total internal reflection as described for example in U.S. Pat. No. 6,594,011 to Kempen, the disclosure of which is incorporated herein by reference in its entirety. Here, the light from a light source is directed through an internal reflection element to reflect off the specimen to be detected.

Figure 4A:
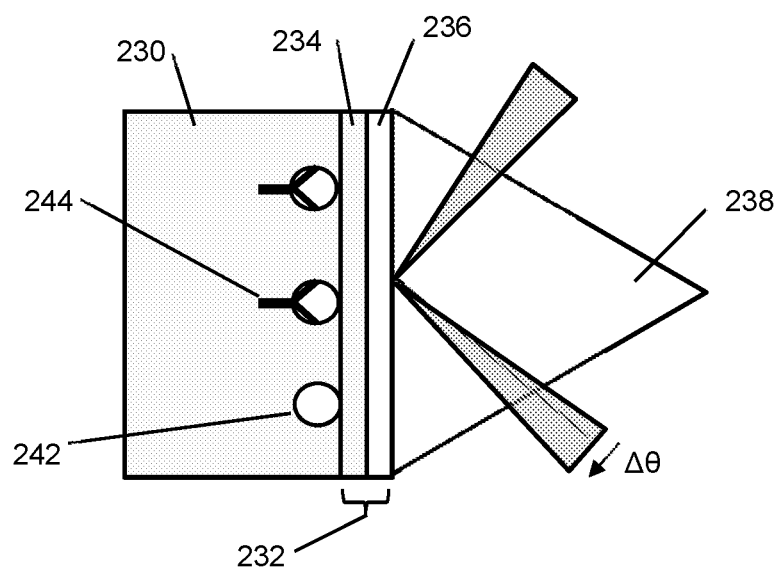
FIGS. 4A-4B are a schematic illustration of an SPR detection system (FIG. 4A), and the output of SPR (FIG. 4B).
Figure 4B:
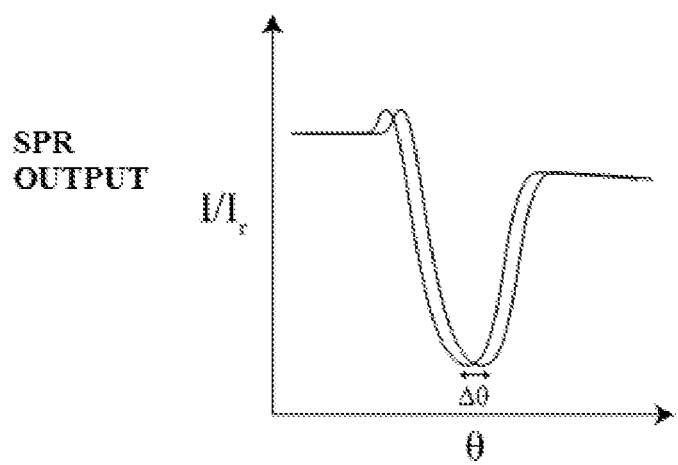

Enhancement of the detection signal can be achieved using SPR spectrometry, illustrated in FIG. 4A. The substrate 232 employed during SPR spectrometry uses a thin metal layer 234 to allow the excitation and propagation of surface plasmons. While one side of the metal layer 234 is in contact with a transparent support structure 236, usually attached to a prism 238 allowing light to couple-in under an oblique angle, the other side of the layer is exposed to the ambient medium 230. As illustrated, an antigen 242 is shown tethered to the metal layer 234 at the ambient medium 230 interface, whereby antibodies (or other binding partners) 244 in solution can bind to the antigen 242. The opposite configuration could also be used. Changes in the optical index of refraction in the ambient by the formation of an adsorbent layer are monitored as a shift in the angle of incidence ($\Delta\theta$) that generates surface plasmon resonance, causing a change of reflected light intensity (see FIG. 4B). For SPR based sensors it is known that an intermediate dielectric layer between the metal film and the probed surface may act as a means to further increase the sensitivity.

The Interferometric Reflectance Imaging sensor ("IRIS"), is described in Ozkumur et al., "Label-free and Dynamic Detection of Biomolecular Interactions for High-throughput Microarray Applications," *Proc Natl Acad Sci USA* 105(23): 7988-7992 (2008) and Ozkumur et al., "Quantification of DNA and Protein Adsorption by Optical Phase Shift," *Biosens Bioelectron* 25(1): 167-172 (2009), the disclosures of which are incorporated herein by reference in their entirety. IRIS uses a silicon chip with a top layer of thick uniform oxide as the solid support for arrayed biomolecules. A tunable laser is incident on the array and reflection spectra are recorded for hundreds of spots simultaneously. The mass at each spot is found by measuring the phase difference between the biolayer and buried mirror reflections in the collected reflection spectra.

The Pierce SearchLight® is a multiplexing sandwich-ELISA system based on chemiluminescent or fluorescent detection of analytes whose respective capture-antibodies are spotted in arrays within each well of a 96-well microplate.

Ray Biotech antibody arrays contain antibodies spotted on either nitrocellulose membrane solid supports or glass slide solid supports. The glass-slide based arrays use fluorescence and need a compatible laser scanner, while the membrane-based arrays use chemiluminescence that can be detected with most Western blot imaging systems.

Each of these label-free and labeled detection formats can accommodate use of the hydrogel particles in accordance with the disclosed procedures and materials.

Regardless of the sensor chip substrate or the detection system in which the substrate is intended to be used, the sensor chip includes a plurality of locations, each having a different probe; in certain embodiments, the same probe will be at multiple locations, but having different concentrations at the different locations.

In various embodiments, the chip can be provided with an array of locations, where different locations have immobilized on the substrate surface hydrogel particles having different concentrations of the same probe molecules, different probe molecules that bind to different sites on the same target molecule, different probe molecules that bind to different target molecules, as well as negative control locations lacking probe molecules, and any number of combinations thereof.

Substrates can be formed using any of a variety of materials. Exemplary materials include, without limitation, silicon such as crystalline silicon, amorphous silicon, or single crystal silicon, oxide glasses such as silicon dioxide, polymers such as polystyrene, and any combination of materials. The materials can also include metal (nano) particles or coatings applied to one or more surfaces of the substrates. In certain embodiments, the surfaces to which the hydrogel particles are applied can have a low surface roughness of less than about 2 nm across the substrate surface, less than about 1 nm across the substrate surface, or less than about 0.5 nm across the substrate surface. In other embodiments, the substrate surface can have higher surface roughness, of greater than about 5 nm across the substrate surface.

The hydrogel particles can be solid hydrogel polymers or they can be hybrid particles, e.g., a hydrogel coating that surrounds a metal or polymer core (Kim and Lee, "Hydrogel-Coated Gold Nanoparticles," *Polymeric Materials: Science and Engineering* 90: 637-638 (2004); Dingenouts et. al., "Observation of the Volume Transition in Thermosensitive Core-Shell Latex Particles by Small-Angle X-Ray Scattering," *Macromolecules* 31: 8912-8917 (1998), the disclosures of which are incorporated herein by reference in their entirety. Hydrogel particles can be formed as small units of crosslinked monomers. Preferably the hydrogel particles are nanoparticles or microparticles (also known as "microgel particles").

The hydrogel particles can be formed of any suitable hydrogel material. Exemplary hydrogel materials include, without limitation, poly-N-isopropylacrylimide (PNIPAM), PNIPAM copolymerized with allyl-iminodiacetic acid, PNIPAM copolymerized with vinylacetic acid, PNIPAM copolymerized with allylamine, PNIPAM grafted with polyethylene glycol-succinic acid, hydroxypropyl cellulose, or a pullulan acetate/sulfonamide conjugate. Different hydrogel materials result in the hydrogel particles being functionalized with a reactive group that facilitates coupling of the probe molecules, as discussed infra. For instance, the PNIPAM copolymerized with vinylacetic acid possess carboxylic acid groups and the PNIPAM copolymerized with allylamine possess amino groups.

Solutions containing the hydrogel particles can be formed using aqueous solutions, including mild buffer solutions, and water. The hydrogel particles can be present in the solution at any suitable concentration that allows for hydrogel particle coverage of the substrate. By way of example, the concentration can range from about $10^8$ to about $10^{14}$ particles per milliliter, with a solids weight percentage between about 0.001% to about 1%. This is exemplary, and deviations from these ranges are contemplated. The optimum concentration for uniform coverage depends on extrinsic and intrinsic factors such as the characteristics of the substrate and the size and area covered by the droplet. For instance, when using a droplet in the picoliter regime, a higher concentration of particles is desirable (e.g., about $10^{11}$ to about $10^{14}$ particles per milliliter).

The probe molecules can be covalently or non-covalently bound to the surface of the hydrogel particles either before or after immobilizing the particles to the surface of the sensor chip. As used herein, a "probe" is any molecule that is capable of binding to a target analyte (i.e., capturing it). Suitable probe molecules include, without limitation, oligonucleotides, nucleic acid aptamers, peptides, proteins, carbohydrates, and non-polymeric small molecules. It is desirable that the probe molecule binds specifically to the analyte of interest.

Exemplary small molecules include, without limitation: avidin, peptido-mimetic compounds, and vancomycin. One class of peptido-mimetic compounds is disclosed in U.S. Pat. No. 6,562,782 to Miller et al., the disclosure of which is incorporated herein by reference in its entirety. A preferred peptido-mimetic compound which binds to lipopolysaccharide is a tetratryptophan ter-cyclopentane as disclosed in the above-noted application to Miller et al. Other peptidomimetic compounds can also be employed.

Exemplary polypeptides include, without limitation, a receptor for cell surface molecule or fragment thereof; a lipid A receptor; an antibody or fragment thereof; peptide monobodies of the type disclosed in U.S. Pat. Nos. 6,673,901 and 7,598,352 to Koide, the disclosures of which are incorporated herein by reference in their entirety; a lipopolysacchardide-binding polypeptide; a peptidoglycan-binding polypeptide; a carbohydrate-binding polypeptide; a phosphate-binding polypeptide; a nucleic acid-binding polypeptide; and polypeptides which bind organic warfare agents such as tabun, sarin, soman, GF, VX, mustard agents, botulinum toxin, *Staphylococcus* entertoxin B, and saitotoxin.

Exemplary nucleic acid molecules can be DNA, RNA, or modified nucleic acids that include 2' or 5'-modified sugars, modified nucleotide bases, or peptide-nucleic acids. The nucleic acids can be any length which is suitable to provide specificity for the intended target. Typically, nucleic acids which do not contain modified nucleotides will be at least about 12 to about 100 nucleotides in length. For nucleic acids which contain modified bases, oligonucleotides should be at least about 7 nucleotides in length, up to about 100 nucleotides in length. Nucleic acid capture molecules can be used for Watson-Crick base-pairing with a complementary or partially complementary target nucleic acid molecule depending on the conditions employed (i.e., low stringency, moderate stringency, or high stringency). Alternatively, nucleic acid aptamer molecules can be used for specific binding to other target molecules, typically proteins, carbohydrates, lipids, etc.

The chemistry used to covalently or non-covalently bind the probe molecules to the hydrogel particles depends upon the available functional groups on the probe and the available functional groups on the hydrogel particles (e.g., amino groups or carboxylic acid groups, as identified above). NETS-mediated or carbodiimide-mediated linkers can be used to facilitate covalent bond formation.

To facilitate non-covalent binding of the probe, the probe molecule can be covalently linked to one member of an affinity binding pair and the hydrogel particle can be linked to another member of the affinity binding pair. Exemplary affinity binding pairs include, without limitation, avidin or streptavidin/biotin interaction or a Protein A/G-immunoglobulin interaction.

Before applying the hydrogel particles to the substrate surface, the surface can optionally be pretreated. In one embodiment, the substrate surface may be treated with a reagent that increases hydrophobicity of the surface. Suitable reagents include sialylating agents which contain one or more hydrophobic sidechains including, but not limited to, any long chain alkane, ring-like structure, or fluorinated silane. Exemplary reagents include, but are not limited to, octadecyltrichlorosilane (OTS), octadecylmethyldiethoxysilane (ODMDES), trimethylchlorosilane (TCS), n-octadecylmethyldiethoxysilane, n-octadecyldimethyldethoxysilane, and n-octadecyltriethoxysilane. A non-covalent surface treatment, such as adsorption of toluene, is also contemplated.

In certain embodiments, the increased hydrophobicity increases the liquid/substrate contact angle, wherein the contact angle is greater than about 50 or 60 degrees, greater than about 70 or 75 degrees, or greater than about 80 or 85 degrees.

In another embodiment, the substrate surface is hydrophobic. In accordance with this aspect, hydrophobic surfaces are characterized by a contact angle of greater than 90 degrees, including greater than about 95 or 100 degrees, and even greater than about 105 degrees.

After selecting the design and substrate for the biosensor device, the hydrogel particles are applied to the substrate. Coating of the hydrogel particles onto the substrate can be performed using techniques well known in the art. Exemplary coating techniques include, but are not limited to, printing, spraying, spotting, depositing, dip-coating, spin-coating, evaporative lithography, and evaporative deposition of the solution onto the substrate. One exemplary method of applying the solution onto the substrate is through piezoelectric printing, which affords reproducible spots on the array.

In one embodiment, the layer of hydrogel particles at the two or more locations is a monolayer of the hydrogel particles.

In another embodiment, multiple layers of hydrogel particles can be applied at each of the two or more locations.

In certain embodiments, the layer of hydrogel particles at the two or more locations is characterized by one or more of: particles having an average diameter of about 50 to about 1000 nm, about 100 to about 900 nm, about 100 to about 500 nm, or about 150 to about 400 nm; particle densities of about $10^8$ to about $10^{14}$ particles/mL, or about $10^9$ to $10^{14}$ particles/mL, or $10^{10}$ to $10^{13}$ particles/mL, which will translate to particle/spot density depending on the volume of the droplet(s) used to form the spots on the resulting array (with the volume typically varying between about 50 picoliters and about 1000 picoliters); a layer thickness of less than 20 nm, less than 15 nm, less than 10 nm, or less than 8, 7, 6, or 5 nm; and a density of probe molecules of about 1 to about $10^6$ per particle, about $10^1$ to $10^5$ per particle, or about $10^2$ to about $10^4$ per particle.

As noted above, the probe molecules can be covalently or non-covalently bound to the surface of the hydrogel particles either before or after the hydrogel particles are immobilized on the substrate surface. Immobilization of the hydrogel particles can be achieved by exposing each location to a solution comprising the hydrogel particles and then allowing the solution to evaporate under controlled conditions, e.g., humidity and temperature, as is well known in the art, whereby the hydrogel particles are uniformly dispersed across the location or spot where the solution is applied. This exposure step can be performed using methods well known in the art including, without limitation, printing, spraying, spotting, or depositing the solution onto the substrate or flowing the solution over the substrate at the one or more sites. In one embodiment, a piezomicroarrayer can be used to dispense solutions onto the chip surface.

After immobilization of the hydrogel particles and probe molecules, it is desirable to wash the substrate surface and/or block the substrate surface to minimize the likelihood that the target molecule or macromolecular structure can be bound non-specifically to the substrate surface. One or more different wash media can be used. In one embodiment, the wash medium contains a blocking agent and optionally one or both of a surfactant and a chelating agent. Exemplary blocking agents include, without limitation, BSA (about 0.25 to about 3%, about 0.5 to about 1.5%, or about 1%), and dilute animal serums. Exemplary surfactants include, without limitation, zwitterionic surfactants of MW 100-10000 Da such as TWEEN®80 (polyoxyethylene (20) sorbitan monooleate), TX100, Pluronics™ (poloxamers), and Brij™ 35/65 (polyoxyethylene alkyl ethers). Exemplary chelating agents include, without limitation, EDTA.

After washing with blocking agent, the substrate surface can be rinsed with water or buffer, and then used directly for target molecule detection. Alternatively, the substrate surface can be dried, e.g., under nitrogen, and stored for future use.

Prior to future use, the dried sensor can be wetted prior to use (i.e., contacting the sensor chip with a sample suspected of containing the target molecule(s)). Wetting of the sensor chip can be achieved using, e.g., water, buffer solutions, polyol solutions, such as those containing trehalose, or glycerol solutions.

Wherever the word "about" is employed herein in the context of dimensions (e.g. particle sizes, diameters, and thickness), amounts (e.g. number of nucleotides in a nucleic acid molecule, weight percent, particle densities, probe densities), temperatures, pressures, times, or concentrations, it will be appreciated that such variables are approximate and as such may vary by ±10%, for example ±5%, ±4%, ±3%, ±2%, or ±1% from the numbers specified herein.

A second aspect relates to a detection system that includes a sensor chip of the first aspect, a light source that is positioned to illuminate the sensor chip, and a detector that is positioned to detect light reflected or emitted from the surface of the sensor chip, and thereby determine whether a target molecule is present in a sample exposed to the surface of the sensor chip.

The light source functions as a source of illumination and may be, for example, a laser and accompanying optics positioned to illuminate the sensor chip surface. Exemplary lasers include, without limitation, argon, cadmium, helium, He—Ne, and nitrogen lasers. The detector is positioned to capture photoluminescent emissions from the sensor chip surface and to detect changes in light reflected or emitted from the sensor chip surface. Exemplary detectors include, without limitation, a charge coupled display, spectrophotometer, photodiode array, photomultiplier tube array, or active pixel sensor array.

The system optionally includes a polarizer positioned between the light source and the sensor chip surface. The system also optionally includes a filter positioned between the light source and the sensor chip surface or, alternatively, between the sensor chip surface and the detector. In FIG. 1, the optional polarizer 14 is shown.

The system may include two or more of the sensor chips, each of the sensor chips being coupled to the light source and the detector.

Another aspect relates to a method for sensing a target molecule in a sample that involves providing a detection system according to the second aspect, directing light at a surface of the sensor chip, contacting the sensor chip with a sample under conditions effective to allow a target molecule in the sample to bind specifically to one of the first and second probe molecules, and detecting light reflected or emitted by sensor chip to identify the presence of a target molecule in the sample.

Samples which can be examined include blood, water, a suspension of solids (e.g., food particles, soil particles, etc.) in an aqueous solution, or a cell suspension from a clinical isolate (such as a tissue homogenate from a mammalian or other patient), cell free extracts, solutions containing candidate drug molecules, and similar types of suspensions or solutions. Samples can also include gases and materials entrained in a gas flow, including reactants present in a vapor phase.

According to this aspect, target molecules may include, without limitation, proteins (including without limitation enzymes, antibodies or fragments thereof), glycoproteins, peptidoglycans, carbohydrates, lipoproteins, a lipoteichoic acid, lipid A, phosphates, nucleic acids which are expressed by certain pathogens (e.g., bacteria, viruses, multicellular fungi, yeasts, protozoans, multicellular parasites, etc.), or organic compounds such as naturally occurring toxins or organic warfare agents, etc. These target molecules can be detected from any source, including food samples, water samples, homogenized tissue from organisms, etc. Moreover, the biological sensor can also be used effectively to detect multiple layers of biomolecular interactions, termed "cascade sensing." Thus, a target, once bound, becomes a probe for a secondary target. This can involve detection of small molecule recognition events that take place relatively far from the substrate's surface.

Presence of the target molecule in the sample will dictate the change in optical property. The specific optical property that is modified will vary depending upon the particular sensing platform used for the detector/sensor chip, but generally includes any one or more of emission or reflectance of light (at a particular wavelength), transmission peak wavelength shift, absorption peak wavelength shift, or refractive index change. To determine whether a change in optical property has occurred, a baseline optical measurement is made prior to exposure to a sample or the optical property is compared to that of an unexposed reference chip. After exposure to the sample, a second optical measurement is made and the first and second measurements are compared. These measurements can also be carried out in real-time, e.g. using a flow cell as described herein or as known in the art and detecting the optical property change as the sample passes over the sensor chip. Typically any change will depend on the size of the target to be recognized and its concentration within the sample.

To quantify the amount of biological target present in a sample, the light source and the detector can both be present in a spectrometer. A computer with an appropriate microprocessor can be coupled to the detector to receive data from the spectrometer and analyze all the data to compare the optical properties before and after exposure of the biosensor to a target molecule.

EXAMPLES

The following examples are provided to illustrate embodiments of the disclosed methods and devices, but they are by no means intended to limit their scope.

Materials and Methods for Examples

Materials.
Poly (N-isopropylacrylamide), bisacrylamide, sodium dodecyl sulfate, allylamine, zero-link or long-chain biotin and O-phthalaldehyde were purchased from Sigma Aldrich. Avidin was purchased from Rockland Immunochemicals. Anti-human tumor necrosis factor alpha IgG (a-TNF-α) and TNF-α were purchased from Biolegend. Silicon substrates with thermally grown oxide both with and without amine reactive surfaces were provided by Adarza BioSystems.

PNIPAM-Co-Allylamine Synthesis.
Poly(N-isopropylacrylamide) co-allylamine microgels were prepared via a free radical precipitation polymerization method modified from the literature (Tsuji et al., *Langmuir* 21:8439-8442 (2005); Pelton, R., *Adv. Colloid Interface Sci.* 85:1-33 (2000); Zhou et al., *Biosens. Bioelectron.* 16:85-95 (2001); Huang et al., *J. Control. Release* 94:303-311 (2004), the disclosures of which are incorporated herein by reference in their entirety). Briefly, (N-isopropylacrylamide) (NIPAM) (0.76 g), bis-acrylamide (BIS) (0.013 g), and allylamine (0.285 g) were dissolved in 50 mL of deionized, glass-distilled H2O (ddH$_2$O) inside a 500 mL 3-neck flask equipped with a nitrogen line, overhead stirrer, and gas outlet. Next, 0.34 mL of aqueous 1% sodium dodecyl sulfate (SDS) was added to the solution and stirred thoroughly. The solution was bubbled with nitrogen for 45 min to remove dissolved oxygen. The mixture was then heated to 60° C., and a solution containing 0.0166 g of ammonium persulfate dissolved in 0.5 mL of ddH$_2$O was injected into the flask to start the reaction. The reaction proceeded for 5 hours, and then the flask was removed from heat and opened to ambient atmosphere while maintaining a constant stir-rate for 15 min. This produced a cloudy suspension, indicating the presence of particles. Lastly, 5 mL of suspended particles were dialyzed for a minimum of 24 hours with 3 exchanges against ddH$_2$O. PNIPAM particles without amine reactivity were synthesized analogously, absent the presence of allylamine. Since it was difficult to determine the concentration of particles in terms of particle number, particles were tracked by their dilution from stocks (e.g. a 1/10 dilution of particles implies stock particles were diluted 10-fold, whereas 1/100 would be 100-fold).

Biotinylation of PNIPAM-Co-Allylamine.

To conjugate biotin to PNIPAM-co-AA particles, 2 mg of long-chain NHS-biotin was dissolved in 100 of DMF, and 20 µL of this solution was added to 10 mL of stock concentration PNIPAM-co-AA particles in modified phosphate buffered saline buffer (mPBS) (10 mM NaH$_2$PO$_4$, 10 mM Na$_2$HPO$_4$, 150 mM NaCl at pH 7.2). The particles were rotated at room temperature for 2 hours and dialyzed extensively against de-ionized glass-distilled water (ddH$_2$O).

Detecting Amine Content Using O-Phthalaldehyde.

Reaction with o-phthalaldehyde was used to measure the amine functional groups present on PNIPAM particles. O-phthalaldehyde (15 mg), β-mercaptoethanol (10 µL), and ethanol (300 µL) were dissolved in 10 mL of 50 mM sodium carbonate buffer (pH=10.5). The reagent was always prepared at most 2 hours prior to use to ensure freshness. A range of allylamine concentrations (50, 5, 0.05, 0.005, and 0.0005 mM) were used to establish a calibration curve; 100 µL of allylamine was prepared at each concentration and mixed with 100 µL of reagent in one well of a 24-well plate. In the same plate, 100 µL of different dilutions (1/10, 1/100, 1/10,000, 1/100,000) of PNIPAM, PNIPAM-co-AA, and PNIPAM-co-AA-biotin with unknown amine content were mixed with 100 µL of working reagent. Samples were equilibrated for 90 seconds, and then absorbance was measured with a spectrophotometer at 410 nm wavelength.

Avidin Conjugation.

A 1/10 dilution of PNIPAM-co-AA-biotin particles in mPBS (pH=7.2) was mixed with an equal volume of 20 mg/mL avidin (final concentration 10 mg/mL) and incubated for 6 hours at 4° C. while rotating on a tube rotator. The particles were then dialyzed extensively against ddH$_2$O using a membrane with molecular weight cutoff of 150 kDa.

Antibody Conjugation.

Biotinylated and avidinylated PNIPAM-co-allylamine diluted 1/35 was pre-mixed with biotinylated antibody at 200 µg/mL (final concentration 100 µg/mL) for at least 6 hours in a 384-well plate. This solution was used directly for printing.

Size Determination by Dynamic Light Scattering.

Particle size measurements were performed using dynamic light scattering with a Malvern ZS90 Zetasizer (Malvern Instruments; Malvern, United Kingdom). Particles were diluted 1/1000 in deionized distilled water before measuring z-average diameter and polydispersity index (PDI). The number of runs was automated by the Malvern software, but was ensured to be always greater than n=3.

Substrate Preparation.

AIR substrates with oxide thickness ranging from 1370 Å-1400 Å with and without amine reactive surfaces were provided by Adarza BioSystems. The contact angles of non-amine reactive AIR substrates were modified by using one of three different silanes: octadecyltrichlorosilane (OTS), octadecylmethyldiethoxysilane (ODMDES), or trimethylchlorosilane (TCS). The silanization procedure is as follows: chips were cleaned by a piranha wash (3:1 H$_2$SO$_4$:H$_2$O$_2$) for 30 minutes and dried with N$_2$. A 2% solution of silane was dissolved in anhydrous toluene and incubated with substrates for 30 minutes, while a control was incubated solely with toluene. Substrates were washed with toluene, dried with N$_2$, placed in an 80° C. oven for 1 hour, and stored in a dry location before use. Static contact angles were measured using a 100-00-115 goniometer (Ramé-Hart Instrument Co.; Succasunna, N.J.), using 2 µL droplets. The contact angle was averaged for each silane from a minimum of 4 data points (different substrates).

Microarray Spot Deposition.

All solutions to be printed were pipetted individually into a 384-well plate at 20 µL volumes. An S3 Sciflexarrayer (Scienion A.G.; Berlin, Germany) with a PDC90 capillary was used to print probes inside a humidity chamber at 60-80% RH. Droplets were approximately 300 pL in volume as measured by the instrument. After deposition, spots were analyzed with an overhead camera to ensure their uniformity and to monitor their drying behavior. Once spots had dried, substrates were removed from the humidity chamber and used for experiments.

Dry Spot Analysis.

Particles were visualized with an AURIGA® CROSSBEAM® SEM-FIB scanning electron microscope (Zeiss; Jena, Germany) at 0.5 kV or an Olympus BX-41 microscope with 500× and 1000× magnifications in brightfield mode. The surface topography of spotted microgels was analyzed with a Solver Next atomic force microscope (NT-MDT; Moscow, Russia). Interparticle distance and particle size calculations using the AFM image were performed using ImageJ (v.1.48k) and custom MATLAB software routines.

Imaging with Arrayed Imaging Reflectometry.

All microarrays were imaged on a prototype AIR imaging system (Adarza BioSystems; NY, USA). Images were acquired for each substrate using custom in-house instrument control software at 10, 50, 100, 250, 500, and 750 millisecond exposure times. Spot intensities were measured using ImageJ (v. 1.48 k) and converted to thicknesses using a best-fit line to a reflectance model (Sriram et al., *Anal. Chem.* 83:3750-3757 (2011), the disclosure of which is incorporated herein by reference in its entirety). Average measurements are composed of at least 4 spots, with errors represented by standard deviations of these measurements.

Target Detection on Immobilized PNIPAM-Co-AA Nanoparticle Microspots.

PNIPAM-co-AA and PNIPAM-co-AA-biotin particles were spotted onto AIR substrates (thermal oxide 135.5 nm) using a piezoelectric microarrayer. After printing the particles, a second layer of spots was placed over the first (overspots) of biotinylated anti-TNF-α antibodies at a concentration of 10 nM in mPBS. After spots had dried, substrates were immediately placed into wells inside of a 24-well plate containing 1% BSA in 50 mM HEPES buffered saline (20 mM HEPES, 150 mM NaCl, pH 7.2) for 30 minutes to block the background from non-specific adsorption. Substrates were then transferred to wells containing 10 nM TNF-α in mPBS buffer and incubated for 1 hour with shaking, followed by mPBS incubation for 30 minutes, and water for 5 minutes before drying and imaging. Substrates were withdrawn after each stage to monitor the thickness change by AIR.

Target Detection Using Antibody Conjugated PNIPAM-Avidin Nanoparticle Microspots.

PNIPAM-avidin and PNIPAM-co-AA-biotin, diluted 1/35, were mixed with biotinylated anti-TNF-α antibodies (200 μg/mL in mPBS), anti-TNF-α antibodies (200 μg/mL in mPBS), or 1% BSA in mPBS. Particles were spotted onto AIR substrates (thermal oxide 135.5 nm) using a piezomicroarrayer as described above. After spots had dried, substrates were immediately placed into wells inside of a 24-well plate containing 1% BSA in 50 mM HEPES buffered saline (20 mM HEPES, 150 mM NaCl, pH 7.2) for 30 minutes to block the background from non-specific adsorption of target. Substrates were then incubated with TNF-α (for selectivity study, concentration was 10 nM, for limit of detection concentration was 1 pg/mL-100 ng/mL in 10-fold increments) overnight at room temperature in a humidity chamber (~80% R.H.) with shaking. Substrates were then washed in mPBS for 30 minutes followed by a 5 minute deionized double distilled water wash before drying and imaging.

Target Detection with PNIPAM-Co-Allylamine-Biotin.

PNIPAM-co-allylamine-biotin particles were spotted onto an ODMDES surface, along with PNIPAM-co-allyamine to serve as a control. After spots had dried, substrates were immediately placed into wells inside of a 24-well plate containing 1% BSA in HBS solution for 30 minutes to block the background from non-specific adsorption. Substrates were transferred to wells containing 100 nM streptavidin and incubated for 1 hour with shaking and then placed in a well containing 10 nM of either the antibody or the biotinylated antibody (10 nM a-hMCP) in PBS for 1 hour with shaking. After IgG incubation, chips were placed in wells containing PBS and shaken for 30 minutes to eliminate any non-specific binding of IgG to the background. Substrates were then transferred to wells containing 10 nM hMCP and incubated for 1 hour with shaking, followed by PBS incubation for 30 minutes, and water for 5 minutes before drying and imaging. Substrates were withdrawn after each stage to monitor the thickness change.

Target Detection with PNIPAM-Co-Allylamine-Biotin-Avidin.

PNIPAM-co-allylamine-biotin-avidin particles were spotted onto an ODMDES surface, along with PNIPAM-co-allylamine-biotin and PNIPAM-co-allylamine to serve as controls. After printing the particles, a second layer of spots was placed over the first (overspots) of the antibodies at a concentration of 10 nM in PBS (anti-TNF-α and a-IL6, with and without biotinylation). After spots had dried, substrates were immediately placed into wells inside of a 24-well plate containing 1% BSA in HBS solution for 30 minutes to block the background from non-specific adsorption. Substrates were then transferred to wells containing either 10 nM TNF-α or IL-6 and incubated for 1 hour with shaking, followed by PBS incubation for 30 minutes, and water for 5 minutes before drying and imaging. Substrates were withdrawn after each stage to monitor the thickness change.

Example 1—PNIPAM-co-allylamine Synthesis

PNIPAM particles with amine functionality were synthesized using precipitation polymerization. Briefly, hydrogel nanoparticles with amine functionality were synthesized in a homogenous radical precipitation polymerization combining (N-isopropylacrylamide) (NIPAM), allylamine (AA), and bis-acrylamide (bisA) monomers to form Poly (N-isopropylacrylamide) and allylamine co-polymerized particles (PNIPAM-co-AA). Particle-bound free amines were reacted with NHS-biotin in a covalent one step process (PNIPAM-co-AA-biotin). As a control, particles made from only NIPAM and bisA were synthesized and contained no free amines. The average diameter and surface charge of the resultant particles were evaluated by dynamic light scattering and zeta potential measurements (FIG. 5). For the size measurements, the average diameter of the PNIPAM-co-allylamine particles are 253.2±59.6 nm with a polydispersity index of 0.055 (FIG. 5, upper graph, gray line). After biotinylation, the particles were 259.7±132.4 nm with a polydispersity index of 0.260 (FIG. 5 upper graph, black line). These data indicate that the particle size distribution broadened after functionalization with NHS-biotin, though the average diameter stayed the same.

To determine the amount of amine present in the particle before and after the functionalization procedure, an o-phthalaldehyde (OPA) assay was performed for different dilutions of PNIPAM-co-allylamine, PNIPAM-co-allylamine-biotin, and PNIPAM.35 The calibration curve for this assay indicated that the colorimetric response had two linear regions (FIG. 6A). A best-fit line was calculated for the intensities, which were in the range of values measured for particles (FIG. 6B).

Figure 7:
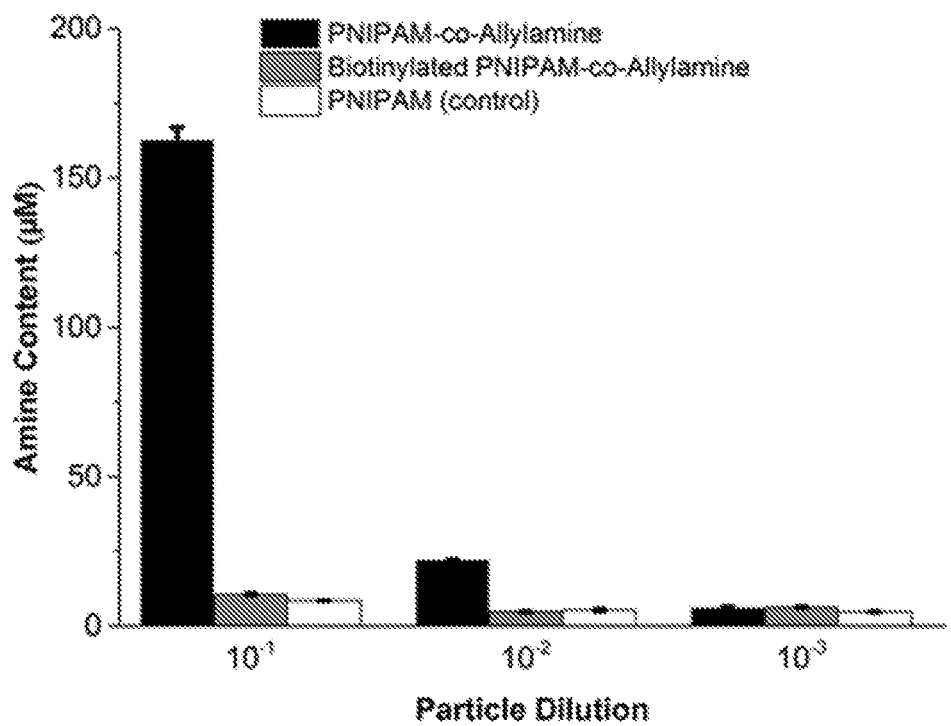
FIG. 7 shows quantification of amines present in 3 different dilutions of PNIPAM (white bar), PNIPAM-co-Allylamine (black bar), and PNIPAM-co-Allylamine conjugated to biotin (gray bar) using an o-phthalaldehyde assay. Fluorescence measurements (n=3) were performed at 460 nm (emission, 360 nm excitation) and averaged. Error bars represent standard deviations from these measurements.

To confirm and quantify successful biotinylation of PNIPAM-co-AA particles, an o-phthalaldehyde (OPA) assay was used to quantify free amines for different dilutions of PNIPAM-co-AA, PNIPAM-co-AA-biotin, and PNIPAM control particles (FIG. 7) (Lee et al., *Int. J. Biochem.* 9:457-467 (1978), the disclosure of which is incorporated herein by reference in its entirety). The number of amines present on PNIPAM-co-allylamine (PNIPAM-co-AA) particles was evaluated to be 163±4.12 μmol/L for particles diluted 1/10, and 22.4±0.01 μmol/L for particles diluted 1/100 (black bar). As expected, the amine content decreased by approximately one order of magnitude. At a higher dilution of 1/1000, the measured amine concentration was not significantly different from that found in the PNIPAM control (white hatched bar), due to reaching the noise floor of the assay at ~5.5 μmol/L. Biotinylated PNIPAM-co-allylamine particles (gray vertical striped bar) had approximately 15 times less amine content compared to PNIPAM-co-AA particles (10.7±0.21 μmol/L) and were found to be only slightly higher than the PNIPAM control (8.6±0.01 μmol/L) suggesting that almost all available amines were biotinylated. More concentrated solutions of particles were not evaluated due to the large volume of particle samples required for the OPA assay.

Figure 8:
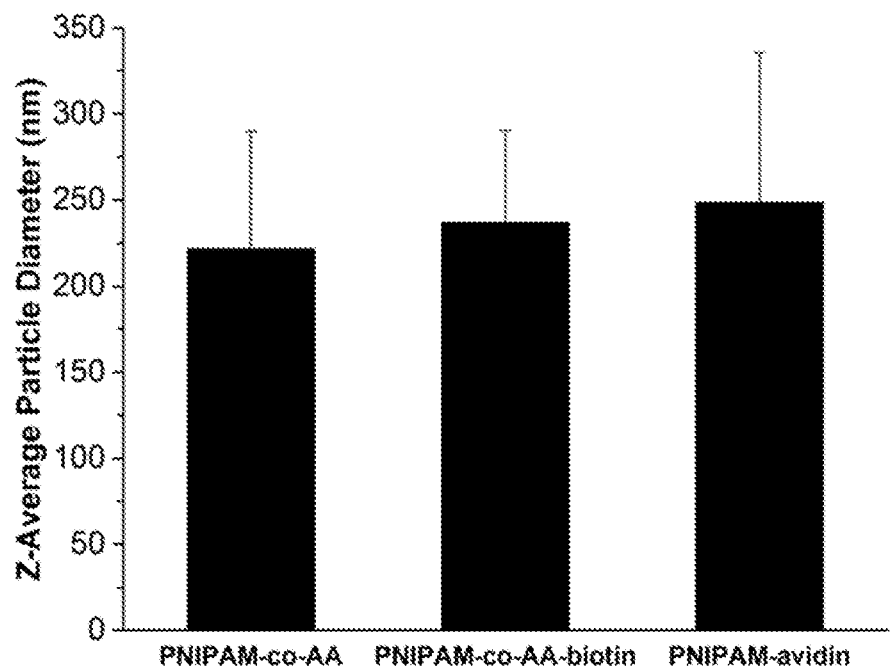
FIG. 8 shows dynamic light scattering evaluation of PNIPAM-co-AA Z-average particle diameters through different stages of conjugation. The original particle (left bar) was covalently biotinylated using an NHS-biotin linker (middle bar). Avidin was then bound to the particle-conjugated biotin (right bar). Error bars represent standard deviations calculated from the square-root of the polydispersity index multiplied by the z-average diameter. The conjugation procedure had no significant effect on particle diameter.

Avidin was conjugated to PNIPAM-co-AA-biotin forming PNIPAM-avidin particles. The average diameters were evaluated by dynamic light scattering at each consecutive step (FIG. 8). PNIPAM-co-AA, PNIPAM-co-AA-biotin, and PNIPAM-avidin particles had z-average diameters of 221±68.3 nm, 237.0±53.5 nm, and 248.5±87.2 nm respectively. The polydispersity indices, which are related to the standard deviations (NanoComposix. *Nanocomposix's Guide to Dynamic Light Scattering Measurement and Analysis*; San Diego, pp. 1-7 (2012), the disclosure of which is incorporated herein by reference in its entirety) were 0.095, 0.051, and 0.123, respectively, indicating that the particles were monodisperse after each step.

Conjugation of biotin and avidin appeared to have no effect on particle size, suggesting that the morphology and size of the particles was constant, with no evidence of either aggregation or precipitation within the solution. This was expected, since PNIPAM nanoparticles are a mesh-like material where significant space within the mesh is taken up by the solvent; conjugation of a protein is believed to have displaced solvent instead of adding thickness.

Example 2—Micro-Arraying Particles

To determine if particles in picoliter droplets would self-assemble upon drying, 450 nm diameter PNIPAM particles were microarrayed using a piezo arrayer onto silicon dioxide substrates equilibrated with toluene. PNIPAM particles were diluted in increments of $2^n$ from 1/2 to 1/2048, micro-arrayed onto silicon dioxide substrates equilibrated with toluene, and imaged with AIR (FIGS. 9A-C). The volume of all dispensed droplets was ~300 pL, with droplet diameters of ~200 µm after deposition. The total number of particles in the droplet varied depending on the dilution. In FIG. 9A, bright regions signify a larger and thicker layer contrasted to the darker and thinner background. As the dilution of particles increased, the position, diameter, and intensity of the dried spots decreased. As expected, well-packed assemblies with variable diameters deposited onto the substrate depending on the concentration of particles within the droplet. At high concentrations (dilutions of 1/2 to 1/8), the dried diameters were relatively constant; however, at higher dilutions they began to vary until they were difficult to discern from the background (dilutions of 1/2048). The particle dilutions from 1/2 to 1/128 appeared to dry uniformly; however, the positions of the spots were erratic. It was determined that the drying was uneven, causing particle assemblies to form at positions off-center from the original location of the droplet. The amount of deviation depended on the particle concentration.

The impact of the underlying surface chemistry on spot morphology was evaluated using silicon dioxide substrates functionalized with different silanes. Chips were functionalized with either octadecyl trichlorosilane (OTS), trimethyl chlorosilane (TCS), octadecylmethyl diethoxysilane (ODMDES), or treated with toluene (control) to create substrate surfaces with three different contact angles. FIG. 9B panels 1-4 show PNIPAM-co-allylamine printed onto $SiO_2$ chips with 137 nm oxide surfaces functionalized with (ODMDES) at 1/40 (panel 1, FIG. 9B), 1/60 (panel 2, FIG. 9B), 1/80 (panel 3, FIG. 9B), and 1/100 (panel 4, FIG. 9B) dilutions. At higher concentrations, spot morphologies contained thick outer rims, which became progressively thinner as the particle concentration decreased.

Substrates were imaged at a higher exposure to highlight the interior arrangement of the spots (FIG. 9C, panels 1-4). All concentrations of particle spots at higher exposures contained concentric circles of brightness within their interiors, indicating that the assemblies contained multilayers or the inter-particle spacing was changing during drying. These data showed that the spot morphology depended on the concentration of particles, which could be easily evaluated on a single substrate using AIR.

PNIPAM particles diluted 1/16 were micro-arrayed onto the substrates with a fixed droplet volume. Brightfield analysis showed drastic differences in sizes and shapes of dried spots and packing behavior of the particles.

Substrates with lower static contact angles had wider spot diameters (FIG. 10, top), which was expected due to the increased spreading of the droplet. The inter-particle spacing increased with lowering contact angle (FIG. 10, bottom). Additionally, there appeared to be little variability throughout the spot on a surface with the highest contact angle, while the other substrates had distinct regions of good and bad packing. This can be best explained by the pinning behaviors of droplets on surfaces with different contact angles, since it alters the interaction of the droplet with the substrate (higher contact angles have less surface/liquid interaction) (Gao et al., "Contact Angle Hysteresis Explained," *Langmuir* 22:6234-7 (2006); Qu et al., "Slippy and Sticky Microtextured Solids," *Nanotechnology* 14:1109-1112 (2003), the disclosures of which are incorporated herein by reference in their entirety). When the interactions between droplet and substrate decrease, pinning occurs less often, and in turn yields more uniform particle depositions within spots. For the purposes of microarraying PNIPAM particles, it was clear that higher contact angles gave better results.

Figure 11:
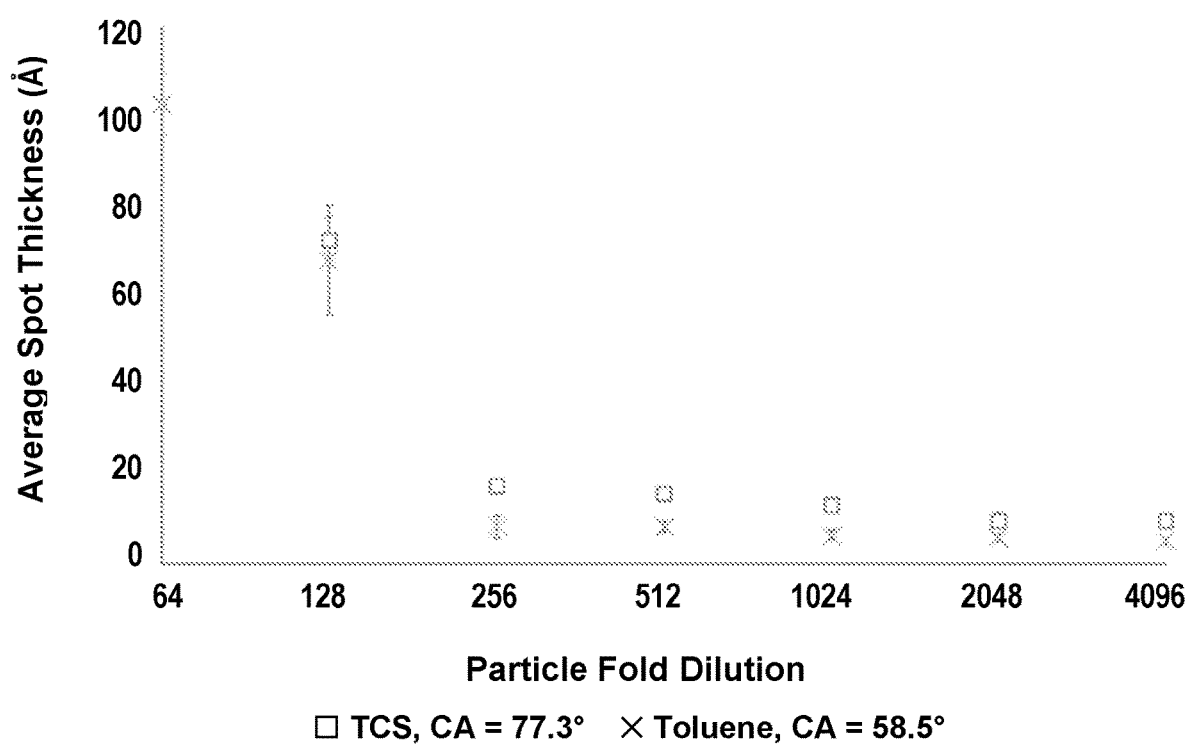
FIG. 11 is a graph showing the effects of average spot thickness for different concentrations of PNIPAM particles on TCS functionalized or toluene washed (control) $SiO_2$ surfaces. Thicknesses are calculated by converting from average intensity values of dried spots measured with AIR. Error bars represent standard deviation of the thickness measured from multiple spots (n=3).

To better understand the relationship between particle concentration and contact angle, intensities of PNIPAM spots were measured at different dilutions on either TCS or toluene substrates, and converted to an average thickness value using AIR. The average thickness was evaluated only for the bright regions to illustrate the difference in particle packing for surfaces at different contact angles. FIG. 11 shows the thickness added by spots to the underlying substrate. The dilution of 1/64 could only be evaluated for the toluene surface due to the TCS intensity readings saturating the CCD, making analysis impossible. The data shows that as the particle dilution increases, the average thickness also decreases. However, at dilutions of 1/256 and higher, spot thicknesses on both the TCS and toluene substrates do not change significantly. This behavior indicates that the inter-particle spacing becomes fixed after a certain concentration. Furthermore, the thickness is greater on substrates with a high contact angle for all concentrations of particle and can be explained by the reduced interaction surface between a water droplet and a high contact angle substrate—more particles will deposit in a smaller area since the contact surface is reduced. Since the volume was fixed in this experiment, particles deposited on hydrophobic surfaces had smaller contact areas, which upon drying yielded closer packed patterns. These data show that the average thickness is reproducible. After a certain threshold, particles pack in a similar manner; however, the spot diameter shrinks as the particle concentration decreases.

Hydrogel nanoparticles were evaluated for their potential application as a substrate for a label-free protein microarray. PNIPAM-avidin particles were diluted 1/70 in 150 mM PBS buffer, and spotted with ~300 pL volumes onto a silicon substrate at 60-80% relative humidity (using a piezomicroarrayer). Droplets were observed to dry into uniform spots ~200 µm in diameter after deposition. Particle packing characteristics inside the spots were assessed by both scanning electron microscopy (SEM) and atomic force microscopy (AFM) (FIGS. 12A-B).

Particles were found to be densely packed with uniform morphology as observed by SEM (FIG. 12A). AFM confirmed that particles were packed in a dense monolayer (FIG. 12B). Image analysis indicated that the particles were separated from the next closest (nearest neighbor) by an average distance of 500±100 nm. A surface scan of a small region indicated that particles dried into flat disc-like shapes 300-400 nm wide and 3-7 nm tall (FIG. 12C), similar to what has been observed by others (Tsuji et al., *Langmuir* 21:8439-8442 (2005); Tsuji et al., *Langmuir* 21:2434-2437 (2005), the disclosures of which are incorporated herein by reference in their entirety). Spot thicknesses and particle distributions within spots were thin and uniform and did not interfere with the performance of the AIR detection system.

Example 3—Making and Testing Antibody Arrays Using PNIPAM-Co-Allylamine

To test the utility of antibody-tagged PNIPAM particles for protein microarray fabrication, a new assay was developed to detect targets using micro arrayed particles on AIR substrates. As with any assay, substrates were required to be washed after incubation with protein to eliminate non-specific binding. However, because particles were non-covalently attached to the surface, it was important to identify a wash procedure that could retain spot morphology. A 1/50 dilution of PNIPAM-co-allylamine-biotin particles was arrayed onto SiO2 substrates functionalized with ODMDES. Substrates were subjected to three different wash procedures to identify a method that retained spot morphology. The first was static buffer incubation for 30 minutes to re-wet dried spots, followed by a 15 minute wash in buffer on a rotation shaker, and then incubation with water for 15 minutes on a rotation shaker. The second procedure was a 30 minute static incubation with 1% bovine serum albumin (BSA), a 15 minute PBS wash on an orbital shaker, and a 15 minute water wash on a rotation shaker. The final procedure was a 30 minute static incubation with a 1% BSA solution, followed by a 15 minute wash in an assay wash buffer solution (PBS containing 0.01% TWEEN® 20 (polyoxyethylene (20) sorbitan monolaurate) and 1 mM EDTA), and a lastly a 15 minute water wash on a rotation station. After the final wash steps, chips were dried with nitrogen and imaged using AIR.

Figure 13A:
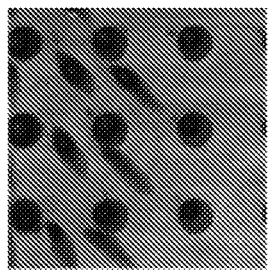
FIGS. 13A-13D show spot morphology of PNIPAM-co-allylamine-biotin after washing surfaces with three different methods.
Figure 13B:
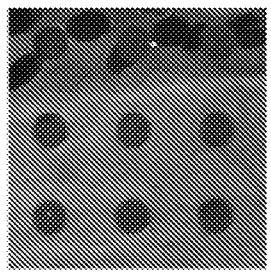
Figure 13C:
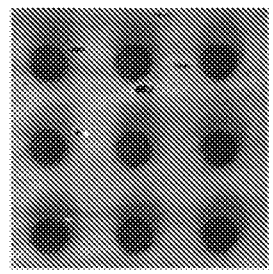
Figure 13D:
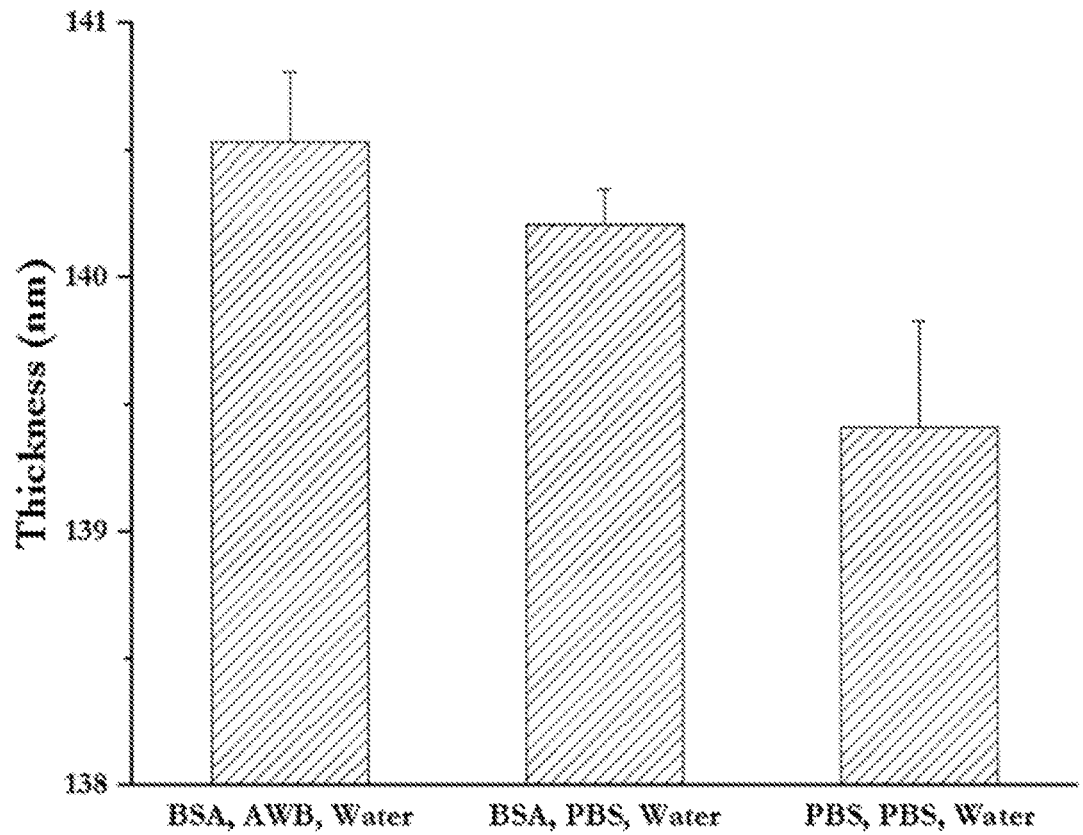

The three wash methods are compared in FIGS. 13A-D. When no BSA was included in the wash, the spots appeared to smear (FIG. 13C), which was expected since there was no protein overlay to keep the particles adhered to the surface. Spots exposed to assay wash buffer (AWB-PBS containing 0.01% TWEEN® 20 and 1 mM EDTA) appeared darker at the centers as indicated by the crescent shapes in the interior (FIG. 13A), indicating that the surfactant preferentially removed particles. However, when spots were incubated with BSA and washed with buffer, the spots had a consistent morphology (FIG. 13B). Spot thicknesses were measured by AIR, and indicated that the thickest spots occurred with the 1% BSA, AWB, and water wash (FIG. 13D). With these data, it was determined that a 1% BSA incubation with a buffer and water wash would retain particle morphologies.

Figure 14A:
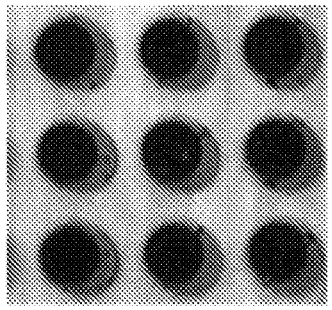
FIGS. 14A-14B are AIR images showing thicknesses of particles incubated with 100 nM streptavidin, followed by incubation with 10 nM anti-human biotinylated TNF-α, and washed with either PBS and water for 15 minutes (FIG. 14A), or with 1% BSA and water (FIG. 14B). Differences in background intensity were observed for BSA blocked chips due to non-specific adsorption and thickening of the substrates.
Figure 14B:
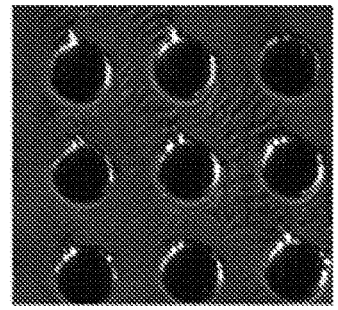

PNIPAM-co-allylamine-biotin particles were micro-arrayed and incubated with streptavidin and conjugated to biotinylated anti-human TNF-α antibody before being washed and imaged by AIR (FIGS. 14A-B). The purpose of this experiment was to confirm the presence of biotin functional groups on the PNIPAM-co-allylamine particles, measure the thickness of antibody bound to particles, and determine if the wash procedures after each step would disrupt the spot morphologies. Wash artifacts appeared in the spots that were not blocked with 1% BSA (FIG. 14A) which disappeared after blocking (FIG. 14B), indicating that a high concentration of nonspecifically adsorbed protein was necessary to fasten the particles in place, which matched the results observed for washing substrates containing particles with no strepavidin and antibody. The 1% BSA also reduced the intensity of the background due to nonspecific adsorption of the protein onto the background substrate. Since the substrate thickness was lower than the particles (so that the spots are at the minimum), the background decreases in intensity as thickness increases.

Hydrogel nanoparticle microspots were evaluated for their ability to perform label-free detection. The cytokine, human tumor necrosis factor alpha (TNF-α), was chosen as a target since its dysregulation is associated with important diseases such as Alzheimer's and various types of cancer. TNF-α is also small (~17 kD) and is generally difficult to quantify with existing fluorescence-based protein microarray technologies, making it an ideal protein to detect with a label-free assay. Both biotinylated and non-biotinylated forms of anti-human TNF-α antibodies were used to selectively capture TNF-α. However, it was expected that only the biotinylated antibody would selectively conjugate onto PNIPAM-avidin.

Figure 15:
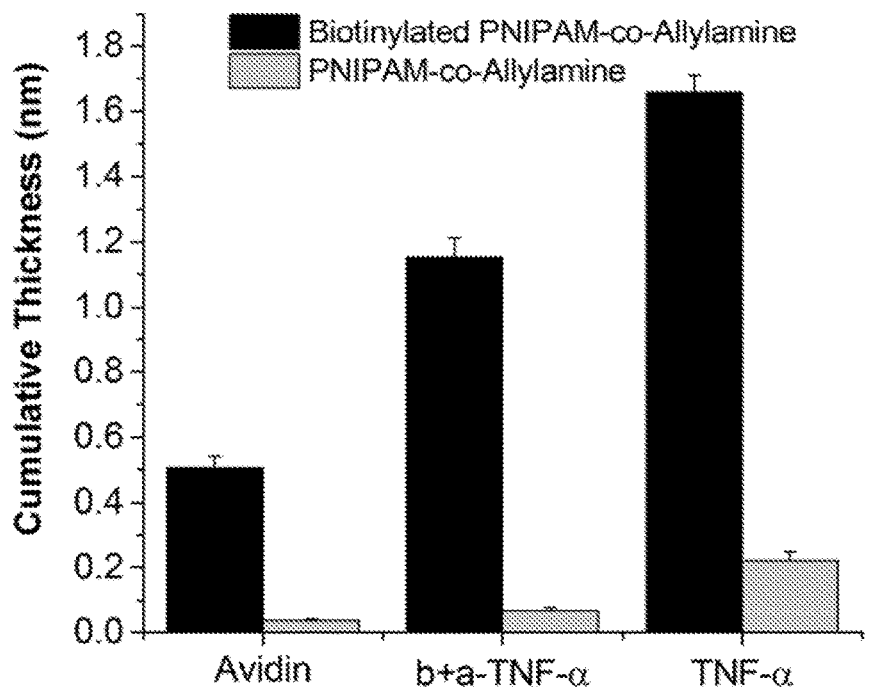
FIG. 15 is a graph showing average spot thickness as measured with AIR on immobilized PNIPAM-co-AA (gray bar) and PNIPAM-co-AA-biotin (black bar) after consecutive staged incubation with avidin, followed by biotinylated anti-human TNF-α (b+a-TNF-α), and ending with TNF-α target detection (TNF-α). Error bars are reported as standard deviations from averaged measurements (n>3).

PNIPAM-co-AA and PNIPAM-co-AA-biotin particles were printed onto protein reactive AIR substrates (silicon with 136 nm of thermally grown oxide), blocked with 1% BSA block, and then incubated with 100 nM avidin, followed by 10 nM biotinylated anti-human TNF-α IgG (b+a-TNF-α), and finally 10 nM human TNF-α (FIG. 15).

The PNIPAM-co-AA spots were used as a control to monitor the nonspecific binding of the different components. The results of the incubation showed that there was specific binding of avidin, biotinylated anti-human TNF-α (b+a-TNF-α) IgG, and TNF-α to the PNIPAM-co-AA-biotin particles with total thickness increases of 0.51±0.04 nm, 1.15±0.06 nm, 1.66±0.05 nm respectively. There non-specific adsorption of the individual components to PNIPAM-co-AA were of 0.04±0.004 nm after avidin, 0.07±0.01 nm after IgG, and 0.2±0.03 after target. Neither of these thicknesses was as large as those seen for PNIPAM-co-AA-biotin. It is likely that the carrier protein (1% BSA) used for IgG and target incubation are what caused the non-specific adsorption since it was present at the highest concentration. The significant increase in thickness for the biotinylated particles indicated that the conjugation between hydrogel particle and biotinylated antibody was successful and could be used to detect targets.

Figure 16:
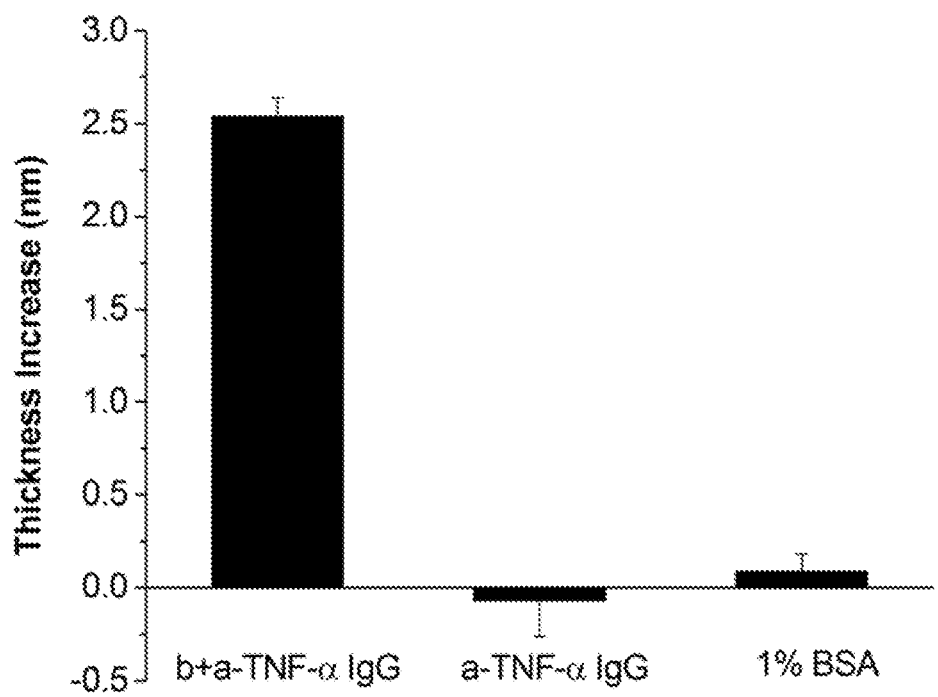
FIG. 16 is a graph showing AIR average measurements (n=35) of avidinylated PNIPAM-co-A nanoparticle spots after incubation with either biotinylated anti-human TNF-α IgG (b+a-TNF-α), anti-human TNF-α IgG (a-TNF-α), and 1% BSA in PBS. Error bars are standard deviations of average measurements.

These results were generated using immobilized PNIPAM-avidin; however, it was also of interest to determine whether PNIPAM-avidin particles could be pre-conjugated with biotinylated antibody and then printed, since this procedure would enable the creation of many particle-antibody pairs from the same starting particle. PNIPAM-avidin particles were pre-mixed with non-biotinylated anti-human TNF-α IgG (a-TNF-α), biotinylated anti-human TNF-α (b+a-TNF IgG), and 1% BSA (as a control), and printed onto AIR substrates. The thicknesses of the resultant spots were measured by AIR (FIG. 16). Results showed that particles selectively interacted with only biotinylated IgG molecules, as shown by the thickness difference (2.5±0.1 nm, versus −0.1±0.0.2 nm). This thickness was also significantly different from the thickness added from only the 1% BSA carrier solution (0.1±0.1 nm). Furthermore, more total antibody was captured when pre-conjugating particles with antibodies rather than immobilizing PNIPAM-avidin first.

Figure 17:
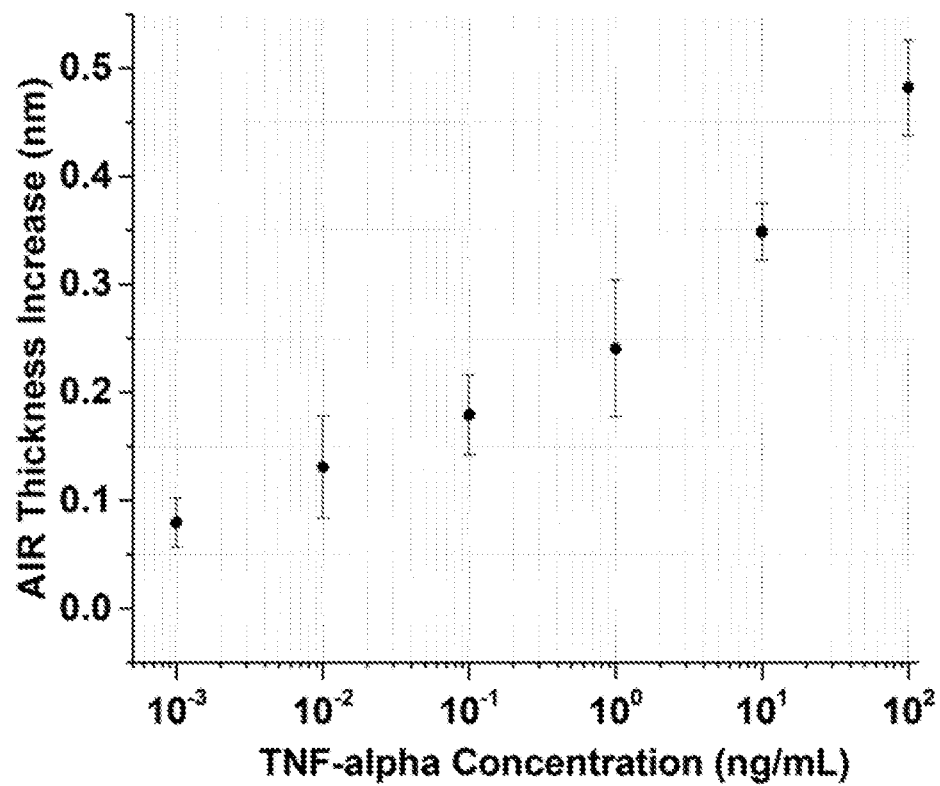
FIG. 17 is a graph showing AIR thickness measurements (n>3) of immobilized PNIPAM-co-AA pre-conjugated with anti-human TNF-α IgG spots, incubated with different concentrations of TNF-α target. Results show an increasing dose-response with concentration of target. Error bars are standard deviations of average measurements.

After confirming that particles could be successfully conjugated to antibodies and used to detect targets, a limit of detection study was performed for TNF-α. PNIPAM-avidin was pre-conjugated to a biotinylated anti-human TNF-α IgG (b+a-TNF-α) and printed with PNIPAM-co-AA-biotin (control) onto AIR substrates (thermal oxide=135.5 nm). Substrates were blocked with 1% BSA and exposed to different concentrations of TNF-α (1 pg/mL–100 ng/mL, 10-fold steps). Thicknesses onto particle spots were measured with AIR, and the non-specific adsorption to PNIPAM-co-AA-biotin was subtracted from the antibody coated particle spots. The results showed a thickness increase with increasing target concentration, and a detection limit of <10 pg/mL, offering similar detection limits to the gold-standard ELISA assays (FIG. 17).

Figure 18:
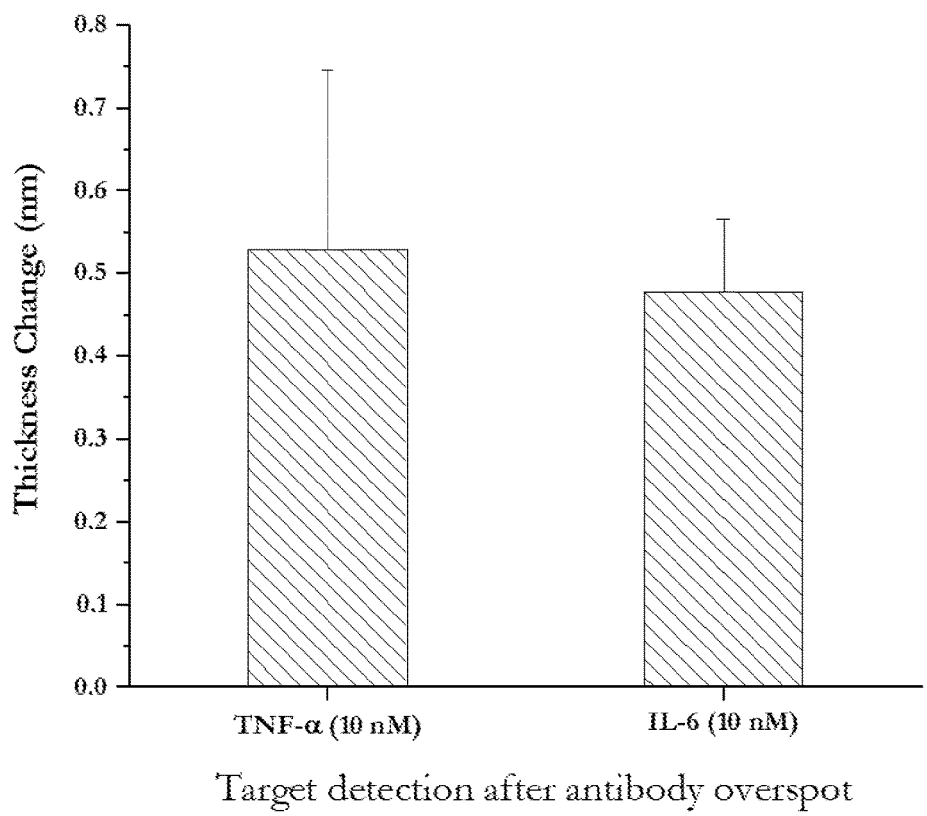
FIG. 18 is a graph showing two different targets that were detected using PNIPAM-co-allylamine-biotin-avidin using two different biotinylated IgG's. In both cases, data was averaged for at least 3 spots, error bars are the standard deviation of the measurement.

The particles specifically interacted with the biotin on the IgG molecules, as shown by the large thickness difference between the biotinylated and non-biotinylated IgG. The carrier protein used for all protein steps also did not add any appreciable thickness to the particles. One of the benefits with AIR is the ability to multiplex and detect multiple targets. To do this, the PNIPAM-co-allylamine-biotin-avidin particles were micro-arrayed onto a substrate, followed by an overspot of a biotinylated antibody specific for either TNF-α or IL-6. Each array was then incubated with 10 nM of one type of target (FIG. 18). Both targets were specifically and successfully detected using this method, though their reported thicknesses are different likely due to the different $K_D$ of the antibody/antigen pairs, since the molecular weight of the two targets is approximately the same (~26 kDa for TNF-α, and ~21 kDa for IL-6). These data indicate that arrays of PNIPAM spots conjugated with different antibodies can be used to detect multiple targets with AIR.

Figures 19A, 19B:
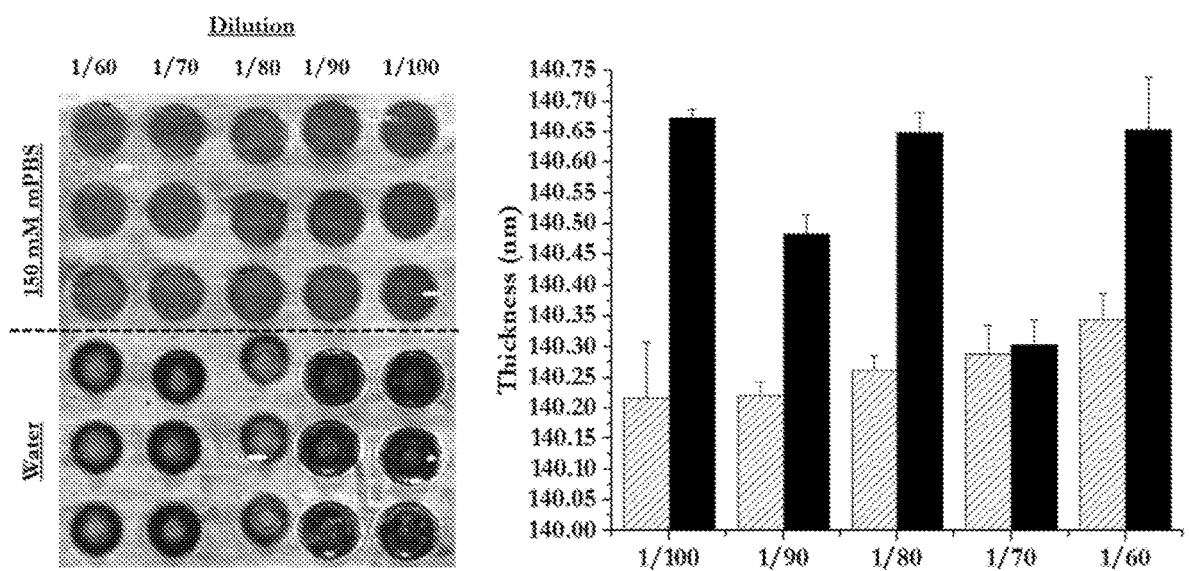
FIGS. 19A-19B show pre-conjugated TNF-α on PNIPAM-co-allylamine-biotin-avidin particles at 5 different dilutions in either mPBS (upper panel, 19A; shaded bars, 19B) or deionized and glass-distilled water ("ddH2O") (lower panel, 19A; black bars, 19B), which was deposited onto a protein reactive substrate using a piezo microarrayer (FIG. 19A). The thickness was evaluated and plotted for each dilution (FIG. 19B). Scale bars are the standard deviation between average intensities of each set of spots (n=3).

After showing that particles could be first immobilized onto a substrate and then equilibrated with antibodies, the next logical progression was to show that particles could be pre-conjugated to those same antibodies and printed directly onto surfaces. For this application, protein reactive substrates were used that were expected to strongly (and covalently) adhere these particles to a surface due to their protein reactive coating. Since these particles could potentially behave different due to the protein reactive surface chemistry of the substrate, the packing morphologies of the PNIPAM-co-allyamine-biotin-avidin particles when pre-incubated with TNF-α were investigated. Particles were diluted in the range 1/100-1/60 in either mPBS (150 mM) or ddH$_2$O and deposited onto protein reactive substrates (FIG. 19A). The spot morphologies were significantly less variable when salt was used, as opposed to only water. Using ImageJ, their thicknesses were measured and plotted (FIG. 19B), where an expected decreasing intensity for increasing particle dilution was observed only for particles containing salt (hatched bars).

To further confirm that that the observed morphology differences via AIR were directly related to particle density differences, SEM images were taken of both types of spots (FIGS. 20A-B). It was clear that the morphology differences in water were the result of particle density differences, where lighter regions in the AIR images corresponded to reduced thickness (FIG. 20A). Furthermore, the SEM confirmed that the addition of the salt allowed for a uniform deposition of particles in the entirety of a spotted region (FIG. 20B).

Figure 21A:
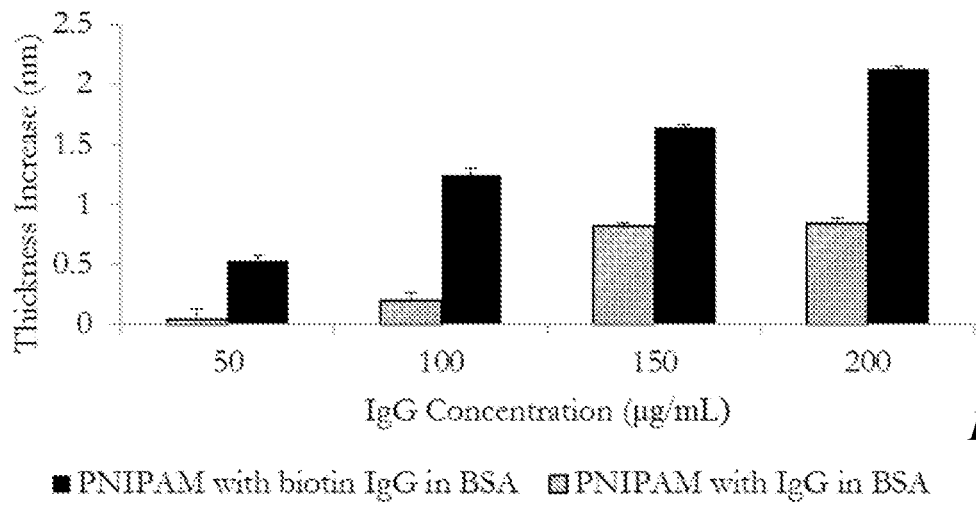
FIGS. 21A-21C are a set of graphs showing a comparison of antibodies that were either pre-conjugated onto PNIPAM particles or immobilized directly onto surfaces. Specificity of biotinylated and unbiotinylated antibody was evaluated on particles (FIG. 21A). A flat surface immobilization was evaluated with and without a BSA blocked surface (FIG. 21B). Since BSA was found to significantly affect antibody measurements for flat surfaces, thicknesses were measured for particles versus flat immobilization in buffer (FIG. 21C).
Figure 21B:
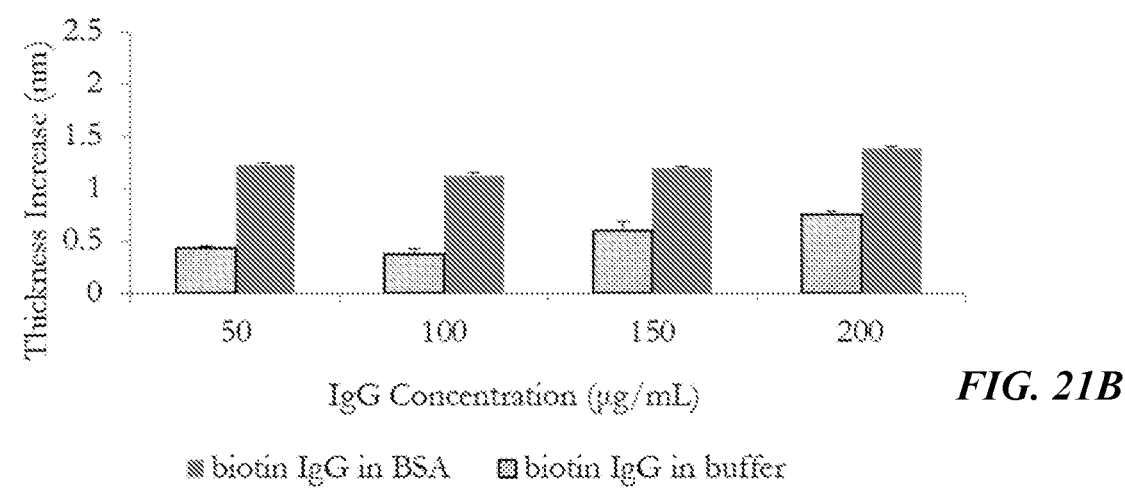
Figure 21C:
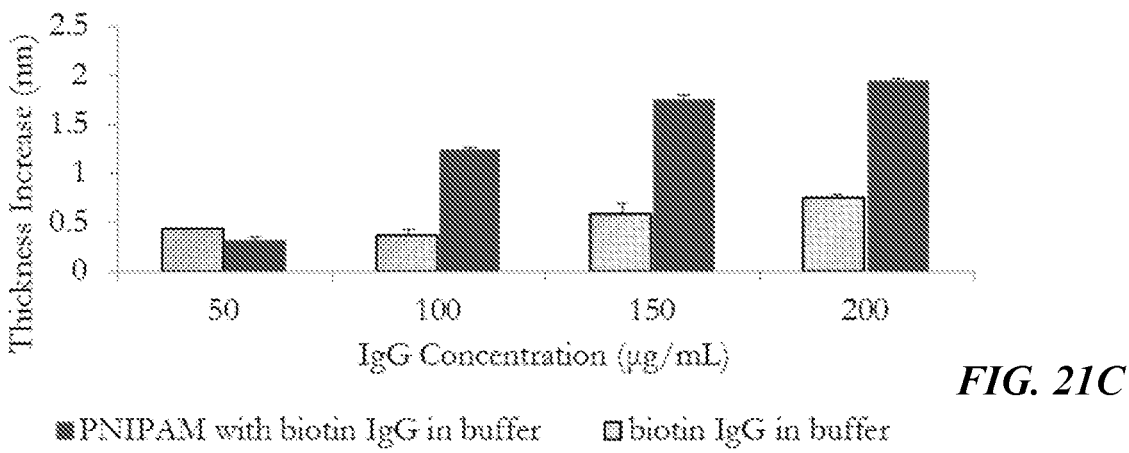

Example 4—Comparing Arrays Using PNIPAM-Co-Allylamine Particles with Conventional AIR Substrates without Particles After finding a solvent that enabled the uniform deposition of antibody conjugated PNIPAM-co-allylamine-biotin-avidin particles, the behaviors of hydrogel nanoparticle antibody spots were compared to conventional AIR substrates where antibody is directly immobilized onto the surface. The specificity was determined by pre-incubating particles with different concentrations of biotinylated or unbiotinylated antibody (FIG. 21A). Biotinylated antibody deposited with the greatest thickness increase (FIG. 21A, solid bar), though an increase was also observed for the unbiotinylated antibody likely due to the underlying protein reactive substrate capturing antibody (FIG. 21A, hatched bar). This hypothesis was further reinforced by the observation that the thickness change of biotinylated IgG spots directly on protein reactive substrates (FIG. 21B, hatched bar) had approximately the same thickness change as the non-specific adsorption onto particles (FIG. 21A, hatched bar). One complication to these experiments was that the BSA blocking step used before detecting targets appeared to add thickness to the antibody spots (FIG. 21B, solid bar) and had the effect of reducing the difference between the antibody spot thicknesses. It is worth noting that there was not a significant change in thickness when blocking the particle spots with BSA (FIG. 21A, solid bar) or buffer (FIG. 21C, solid bar), suggesting that the particles blocked its adsorption to the surface. To compare the total amount of antibody bound to flat versus hydrogel surfaces, their thicknesses in buffer were compared to one another. The results showed that significantly more antibody was bound to the surface when using particles compared to the flat surface (FIG. 21C). Furthermore the change in thickness as a function of incubating IgG concentration was highest for particle spots suggesting that antibody thicknesses could be more easily tuned than with flat surfaces. In conclusion, these results showed that using antibodies pre-conjugated to particles had superior performance characteristics compared to flat surface immobilization techniques.

Discussion of Examples

To improve the probe density for nanoscale biosensors, three dimensional hydrogel protein networks were developed from the bottom-up. Currently available hydrogel polymerization techniques interfere with the sensing modalities of many label-free biosensors. As an alternative, a hydrogel nanoparticle deposition technique was developed, which utilized the strong binding capability of streptavidin/biotin to generically couple probe molecules to particles. It was demonstrated that these nanoparticles form uniform and reproducible monolayers that are less than 10 nm thin, and that they can be arrayed in a multiplexed manner on a surface. Using a highly sensitive biosensor, a large increase in target detection and dynamic range of the device was shown when compared with 2D immobilization strategies. In the future it will be possible to develop simpler conjugation strategies to quickly generate a particle/probe conjugate library. This strategy should work equally well with other nanoscale sensors, since their sensitivities should also improve with an increase in probe density.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims

What is claimed:

1. A sensor chip for detecting a target molecule in a sample, the sensor chip comprising:
a substrate comprising a coating compatible with label-free, optical detection of probe molecule-target molecule binding, the substrate and coating each having a refractive index and the coating having a surface and a thickness; and a monolayer of hydrogel particles immobilized on the coating surface at two or more locations on the surface, wherein the hydrogel particles at a first location comprise a plurality of first probe molecules bound to the particles and the hydrogel particles at a second location comprise a plurality of second probe molecules bound to the particles;

wherein the sensor chip is an Arrayed Imaging Reflectometry sensor chip, the substrate is a silicon substrate, and the coating is a silicon dioxide coating having a surface roughness of less than about 0.5 nm across the substrate surface, and wherein, due to the combination of the silicon substrate and silicon dioxide coating refractive indices and silicon dioxide coating thickness, the structure of the sensor chip affords, upon illumination of the sensor chip with s-polarized light having a particular wavelength and a particular angle of incidence, a near zero background reflectivity in the absence of probe molecule-target molecule binding at any of the two or more locations and increased reflectivity in the presence of probe molecule-target molecule binding at any of the two or more locations.

2. The sensor chip according to claim 1, wherein the hydrogel particles are non-covalently attached to the substrate surface.

3. The sensor chip according to claim 1, wherein the hydrogel particles comprise poly-N-isopropylacrylimide (PNIPAM), PNIPAM copolymerized with allyl-iminodiacetic acid, PNIPAM copolymerized with vinylacetic acid, PNIPAM copolymerized with allylamine, PNIPAM grafted with polyethylene glycol-succinic acid, hydroxypropyl cellulose, or a pullulan acetate/sulfonamide conjugate.

4. The sensor chip according to claim 1, wherein one or both of the first and second probe molecules are covalently bound to the hydrogel particles of first and second locations, respectively.

5. The sensor chip according to claim 1, wherein one or both of the first and second probe molecules are non-covalently bound to the hydrogel particles of first and second locations, respectively.

6. The sensor chip according to claim 1, wherein the monolayer of hydrogel particles at the two or more locations is characterized by one or more of:
- particles having an average diameter of about 50 nm to about 1000 nm;
- particle densities of about $10^8$ to about $10^{14}$ particles/mL per volume applied to each location;
- a monolayer thickness of less than 10 nm; and
- a density of first and/or second probe molecules of about 1 to about $10^6$ per particle.

7. The sensor chip according to claim 1, wherein the first and second probe molecules are independently selected from the group consisting of oligonucleotides, nucleic acid aptamers, peptides, proteins, and non-polymeric small molecules.

8. The sensor chip according to claim 1, wherein the sensor chip is capable of detecting the probe molecule-target molecule binding while the monolayer of hydrogel particles remain immobilized on the substrate surface.

9. A detection system comprising:
- a sensor chip according to claim 1;
- a light source that is positioned to illuminate the sensor chip with s-polarized light; and
- a detector that is positioned to detect light reflected or emitted from the surface of the sensor chip, and thereby determine whether a target molecule is present in a sample exposed to the surface of the sensor chip.

10. A method for sensing a target molecule in a sample, the method comprising:
- providing a detection system according to claim 9;
- directing s-polarized light at a surface of the sensor chip;
- contacting the sensor chip with a sample under conditions effective to allow a target molecule in the sample to bind specifically to one of the first and second probe molecules; and
- detecting light reflected or emitted by sensor chip to identify the presence of a target molecule in the sample.

11. The method according to claim 10, wherein the sensor chip of the provided detection system is dry and the method further comprises wetting the sensor chip prior to said contacting.

* * * * *